United States Patent [19]

Fischer et al.

[11] Patent Number: 5,589,469
[45] Date of Patent: Dec. 31, 1996

[54] SUBSTITUTED 1H-3-ARYL-PYRROLIDINE-2,4-DIONE DERIVATIVES

[75] Inventors: Reiner Fischer, Monheim; Bernd-Wieland Krüger, Bergisch Gladbach; Thomas Bretschneider, Siegburg; Christoph Erdelen, Leichlingen; Ulrike Wachendorff-Neumann, Monheim; Klaus Lürssen, Bergisch Gladbach; Hans-Joachim Santel, Leverkusen; Robert R. Schmidt, Bergisch Gladbach, all of Germany

[73] Assignee: Bayer Aktiengesellschaft, Leverkusen, Germany

[21] Appl. No.: 483,913

[22] Filed: Jun. 7, 1995

Related U.S. Application Data

[63] Continuation of Ser. No. 166,669, Dec. 14, 1993, abandoned, which is a continuation of Ser. No. 901,051, Jun. 19, 1992, abandoned.

[30] Foreign Application Priority Data

Jun. 28, 1991 [DE] Germany ............ 41 21 365.3

[51] Int. Cl.$^6$ ............ A01N 43/36; A01N 57/16; C07D 207/273; C07F 9/572
[52] U.S. Cl. ............ 514/91; 514/425; 544/141; 548/413; 548/544; 504/283
[58] Field of Search ............ 548/544, 413; 514/425, 91

[56] References Cited

U.S. PATENT DOCUMENTS

| | | | |
|---|---|---|---|
| 4,925,868 | 5/1990 | Terao et al. | 548/544 |
| 5,045,560 | 9/1991 | Fisher et al. | 548/544 |
| 5,258,527 | 11/1943 | Krauskopf et al. | 548/543 |

FOREIGN PATENT DOCUMENTS

| | | |
|---|---|---|
| 0415185 | 8/1990 | European Pat. Off. |
| 0442077 | 12/1990 | European Pat. Off. |
| 0456063 | 4/1991 | European Pat. Off. |
| 4032090 | 10/1990 | Germany |

OTHER PUBLICATIONS

Bertram, Chemical Abstracts, vol. 115, No. 207,850 (1991) Abstract of EP 442,077.
S. Suzuki et al, "Studies on Antiviral Agents . . . ", Chem. Pharm. Bull. 15, (1967), pp. 1120–1122.
R. Schmierer et al, "Cyclisierung von N–Acylalanin–. . . ", Liebigs Ann. Chem. (1985) pp. 1095–1098.
"Reactions of Aliphatic Acid Chlorides", Chem. Reviews, V. 52 (1953), pp. 269–277.
H. R. Harrison et al, "Use of molecular sieves in the methyl esterification . . . ", Chem. and Ind., (1968), p. 1568.

W. J. Spillane et al, "Versatile Synthesis of Sulphamate Esters by . . . ", J. Chem. Soc. (3), (1982), pp. 677–679.

*Primary Examiner*—Robert W. Ramsuer
*Attorney, Agent, or Firm*—Sprung Horn Kramer & Woods

[57] ABSTRACT

There are provided novel substituted 3-aryl-pyrrolidine-2,4-dione derivatives of the formula (I)

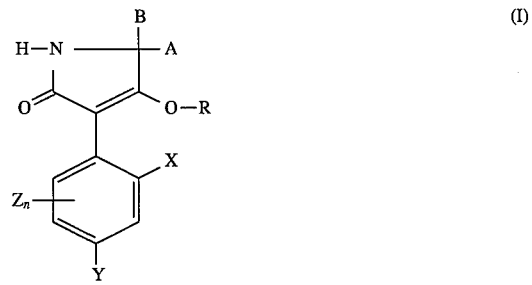

in which
X represents alkyl, halogen or alkoxy,
Y represents hydrogen, alkyl, halogen, alkoxy or halogenoalkyl,
Z represents alkyl, halogen or alkoxy,
n represents a number from 0–3,
A represents hydrogen, or represents alkyl, alkoxyalkyl or alkylthioalkyl, each of which is optionally substituted by halogen, cycloalkyl which is optionally interrupted by hetero atoms, or represents aryl, arylalkyl or hetaryl, each of which is optionally substituted by halogen-, alkyl-, halogenoalkyl-, alkoxy- or nitro-,
B represents hydrogen, alkyl or alkoxyalkyl,
or in which
A and B together with the carbon atom to which they are bonded form an optionally substituted saturated or unsaturated cycle which can be interrupted by oxygen and/or sulphur.
R represents the groups

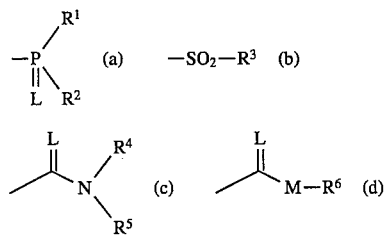

in which L, M as well as $R^1, R^2, R^3, R^4, R^5$ and $R^6$ have the meaning given in the text of the application.

The new compounds (I) have highly pronounced insecticidal, acaricidal and herbicidal properties.

8 Claims, No Drawings

SUBSTITUTED 1H-3-ARYL-PYRROLIDINE-2,4-DIONE DERIVATIVES

This application is a continuation application Ser. No. 08/166,669, filed on Dec. 14, 1993 now abandoned which is a continuation of application Ser. No. 07/901,051, filed on Jun. 19, 1992 now abandoned.

The invention relates to new substituted 3-aryl-pyrrolidine-2,4-dione derivatives, to a plurality of processes for their preparation, and to their use as insecticides, acaricides and herbicides.

3-Acyl-pyrrolidine-2,4-diones have previously been described as having pharmaceutical properties (S. Suzuki et al Chem. Pharm. Bull. 15 1120 (1967)). Furthermore, N-phenyl-pyrrolidine-2,4-diones were synthesised by R. Schmierer and H. Mildenberger,Liebigs Ann. Chem. 1985 1095. A biological activity of these compounds has not been described.

EP-A 0,262,399 discloses compounds (3-aryl-pyrrolidine-2,4-diones) which have a similar structure but which were not known as having a herbicidal, insecticidal or acaricidal action.

DE-A 3,525,109 discloses 1 H-3-arylpyrrolidine-2,4-diones which have a similar structure and which are used as intermediates for the syntheses of dyestuffs.

New substituted 3-aryl-pyrrolidine-2,4-dione derivatives have now been found which are represented by the formula (I)

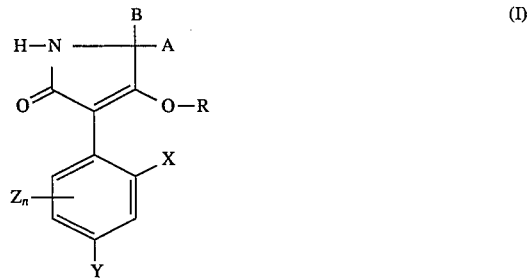

in which

X represents alkyl, halogen or alkoxy,

Y represents hydrogen, alkyl, halogen, alkoxy or halogenoalkyl,

Z represents alkyl, halogen or alkoxy, n represents a number from 0–3,

A represents hydrogen, or represents alkyl, alkoxyalkyl or alkylthioalkyl, each of which is optionally substituted by halogen, cycloalkyl which is optionally interrupted by hetero atoms, or represents aryl, arylalkyl or hetaryl, each of which is optionally substituted by halogen, alkyl, halogenoalkyl, alkoxy or nitro, B represents hydrogen, alkyl or alkoxyalkyl, or in which A and B together with the carbon atom to which they are bonded forman optionally substituted saturated or unsaturated cycle which can be interrupted by oxygen and/or sulphur, R represents the groups

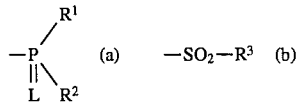

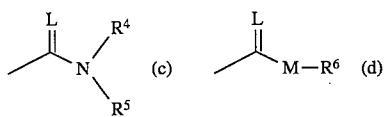

in which

L and M represent oxygen or sulphur, and L and M do not simultaneously represent oxygen, $R^1$, $R^2$ and $R^3$ independently of each other represent alkyl, alkoxy, alkylamino, dialkylamino, alkylthio, alkenylthio, alkinylthio and cycloalkylthio, each of which is optionally substituted by halogen, and represent in each case optionally substituted phenyl, benzyl, phenoxy or phenylthio, $R^4$ and $R^5$ independently of each other represent hydrogen, or represent alkyl, alkenyl, alkoxy or alkoxyalkyl, each of which is optionally substituted by halogen, or represent optionally substituted phenyl or optionally substituted benzyl, or $R^4$ and $R^5$ together represent an alkenyl radical which is optionally interrupted by oxygen, $R^6$ represents alkyl which is optionally substituted by halogen and which can be interrupted by oxygen, or represents phenyl which is optionally substituted by halogen, halogenoalkyl or alkoxy, or represents benzyl which is optionally substituted by halogen, halogenoalkyl, alkyl and alkoxy, or represents alkenyl or alkinyl, and the pure enantiomeric forms of compounds of the formula (I).

Taking into account the various meanings (a), (b), (c) and (d) of group R of the general formula (I), the following main structures (Ia) to (Id) result:

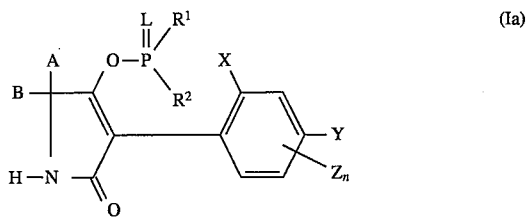

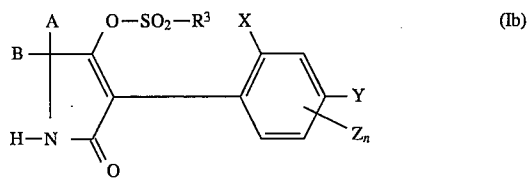

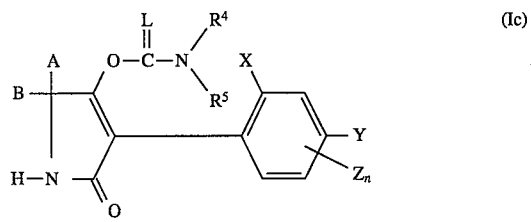

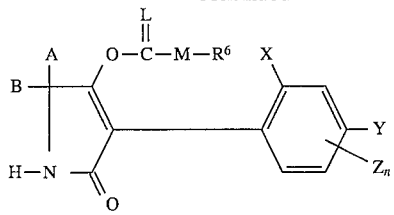
(Id)

in which A, B, L, M, X, Y, $Z_n$, $R^1$, $R^2$, $R^3$, $R^4$, $R^5$ and $R^6$ have the abovementioned meanings.

Furthermore, it has been found that 3-aryl-pyrrolidone-2,4-dione derivatives of the formula (Ia)

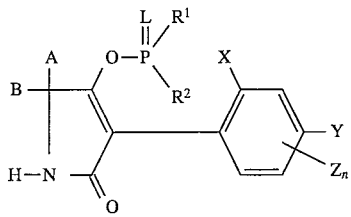
(Ia)

in which A, B, L, X, Y, Z, $R^1$, $R^2$ and n have the abovementioned meaning are obtained when A) 3-aryl-pyrrolidine-2,4-diones of the formula (II) or the enols thereof

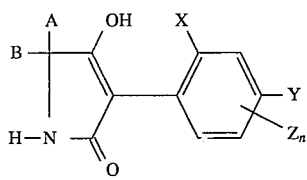
(II)

in which A, B, X, Y, Z and n have the abovementioned meaning are reacted with phosphorus compounds of the general formula (III)

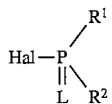
(III)

in which
L, $R^1$ and $R^2$ have the abovementioned meaning and Hal represents halogen, in particular chlorine and bromine, if appropriate in the presence of a diluent, if appropriate in the presence of an acid-binding agent and if appropriate in the presence of a phase-transfer catalyst.

B) Furthermore, it has been found that compounds of the formula (Ib)

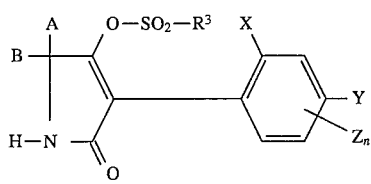
(Ib)

in which A, B, X, Y, Z, $R^3$ and n have the abovementioned meaning are obtained when compounds of the formula (II)

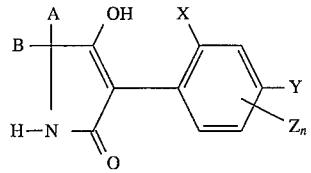
(II)

in which A, B, X, Y, Z and n have the abovementioned meaning are reacted with sulphonyl chlorides of the general formula (IV)

$$R^3-SO_2-Cl \qquad (IV)$$

in which
$R^3$ has the abovementioned meaning, if appropriate in the presence of a diluent and if appropriate in the presence of an acid-binding agent.

C) Furthermore, it has been found that compounds of the formula (Ic)

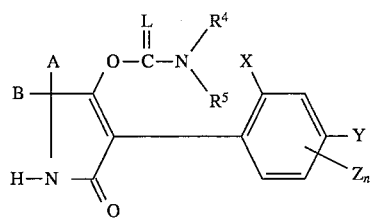
(Ic)

in which A, B, L, X, Y, Z, $R^4$, $R^5$ and n have the abovementioned meaning, are obtained when compounds of the formula (II)

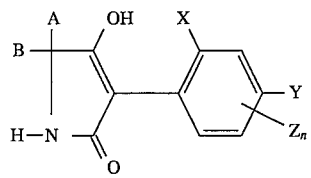
(II)

in which A, B, X, Y, Z and n have the abovementioned meaning are either

α) reacted with isocyanates of the general formula (V)

$$R^4-N=C=O \qquad (V)$$

in which $R^4$ has the abovementioned meaning, if appropriate in the presence of a diluent and if appropriate in the presence of a catalyst, or are β) reacted with carbamic acid chlorides or thiocarbamic acid chlorides of the general formula (VI)

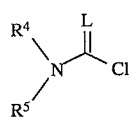
(IV)

in which L, $R^4$ and $R^5$ have the abovementioned meaning, if appropriate in the presence of a diluent and if appropriate in the presence of an acid-binding agent.

D) Furthermore, it has been found that compounds of the formula (Id)

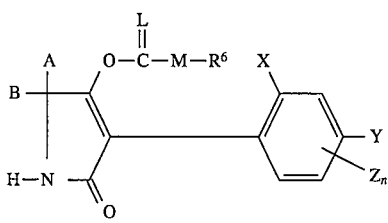

(Id)

in which A, B, L, M, R⁶ X, Y, Z, and n have the abovementioned meaning, are obtained when compounds of the formula (II)

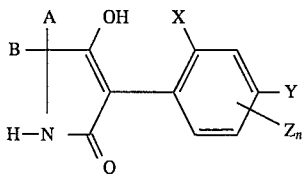

(II)

in which A, B, X, Y, Z and n have the abovementioned meaning

α) are reacted with chloromonothioformic esters, chloroformic thioesters or chlorodithioformic esters of the general formula VII

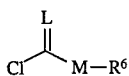

(VII)

in which L, M and R⁶ have the abovementioned meaning, if appropriate in the presence of a diluent and if appropriate in the presence of an acid-binding agent, or β) are reacted with carbon disulphide and subsequently with alkyl halides of the general formula VIII R⁶-Hal                                                    (VIII)

in which
R⁶ has the abovementioned meaning and
Hal represents chlorine, bromine or iodine.

Surprisingly, it has been found that the new substituted 1 H-3-aryl-pyrrolidine-2,4-dione derivatives of the formula (I) are distinguished by outstanding insecticidal, acaricidal and herbicidal actions.

Preferred substituted 1 H-3-aryl-pyrrolidine-2,4-dione derivatives of the formula (I) are those in which X represents $C_1$–$C_6$-alkyl, halogen or $C_1$–$C_6$-alkoxy, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, n represents a number from 0–3, A represents hydrogen or in each case straight-chain or branched $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, $C_1$–$C_8$-polyalkoxy-$C_2$–$C_8$-alkyl and $C_1$–$C_{10}$-alkylthio-$C_2$–$C_8$-alkyl, each of which is optionally substituted by halogen, or represents cycloalkyl which has 3–8 ring atoms and which can be interrupted by oxygen and/or sulphur, or represents aryl, hetaryl or aryl-$C_1$–$C_6$-alkyl, each of which is optionally substituted by halogen, $C_1$–$C_6$-alkyl, $C_1$–$C_6$-haloalkyl, $C_1$–$C_6$-alkoxy or nitro, B represents hydrogen or in each case straight-chain or branched $C_1$–$C_{12}$-alkyl or $C_1$–$C_8$-alkoxyalkyl, or in which A and B together with the carbon atom to which they are bonded form a 3- to 8-membered saturated or unsaturated ring which can be interrupted by oxygen and/or sulphur and which can be substituted by in each case optionally halogenated alkyl, alkoxy or phenyl and halogen, R represents the groups

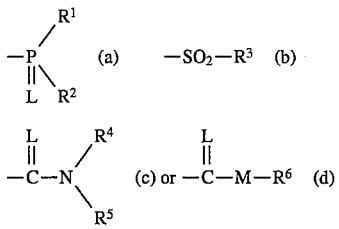

in which

L and M in each case represent oxygen or sulphur and L and M do not simultaneously represent oxygen, $R^1$, $R^2$ and $R^3$ independently of each other represent $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_2$–$C_5$-alkenylthio, $C_2$–$C_5$-alkinylthio and $C_3$–$C_7$-cycloalkylthio, each of which is optionally substituted by halogen, or represent phenyl, benzyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^4$ and $R^5$ independently of each other represents $C_1$–$C_{20}$-alkyl, $C_1$–$C_{20}$-alkoxy, $C_2$–$C_8$alkenyl or $C_1$–$C_{20}$-alkoxy-$C_1$–$C_{20}$-alkyl, each of which is optionally substituted by halogen, or represents phenyl which is optionally substituted by halogen, $C_1$–$C_{20}$-halogenoalkyl, $C_1$–$C_{20}$-alkyl or $C_1$–$C_{20}$-alkoxy, or represents benzyl which is optionally substituted by halogen, $C_1$–$C_{20}$-alkyl, $C_1$–$C_{20}$-halogenoalkyl or $C_1$–$C_{20}$-alkoxy, or together represent a $C_2$–$C_6$-alkylene ring which is optionally interrupted by oxygen, $R^6$ represents $C_1$–$C_{20}$-alkyl which is optionally substituted by halogen and which can be interrupted by oxygen or represents phenyl which is optionally substituted by halogen, $C_1$–$C_{20}$-halogenoalkyl or $C_1$–$C_{20}$-alkoxy, or represents benzyl which is optionally substituted by halogen, $C_1$–$C_{20}$-halogenoalkyl or $C_1$–$C_{20}$-alkoxy, or represents $C_2$–$C_8$-alkenyl or $C_2$–$C_5$-alkinyl, and the pure enantiomeric forms of compounds of the formula (I).

Particularly preferred compounds of the formula (I) are those in which

X represents $C_1$–$C_4$-alkyl, halogen or $C_1$–$C_4$-alkoxy,

Y represents hydrogen, $C_1$–$C_6$-alkyl, halogen, $C_1$–$C_4$-alkoxy or $C_1$–$C_2$-halogenoalkyl, Z represents $C_1$–$C_4$-alkyl, halogen or $C_1$–$C_4$-alkoxy, n represents a number from 0–3, A represents hydrogen or in each case straight-chain or branched $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, $C_1$–$C_6$-polyalkoxy-$C_2$–$C_6$-alkyl and $C_1$–$C_8$-alkylthio-$C_2$–$C_6$-alkyl, each of which is optionally substituted by halogen, or represents cycloalkyl having 3–7 ring atoms which can be interrupted by 1–2 oxygen and/or sulphur atoms, or represents aryl, hetaryl or aryl-$C_1$–$C_4$-alkyl, each of which is optionally substituted by halogen, $C_1$–$C_4$-alkyl, $C_1$–$C_4$-haloalkyl, $C_1$–$C_4$-alkoxy or nitro, represents hydrogen or in each case straight-chain or branched $C_1$–$C_{10}$-alkyl or $C_1$–$C_6$-alkoxyalkyl, or in which A and B together with the carbon atom to which they are bonded form a 3-to 7-membered saturated or unsaturated ring which can be substituted by $C_1$–$C_6$-alkyl, $C_1$–$C_6$-alkoxy, $C_1$–$C_3$-haloalkyl, $C_1$–$C_3$-haloalkoxy, fluorine, chlorine and substituted phenyl, and which can be interrupted by oxygen and/or sulphur, R represents the groups

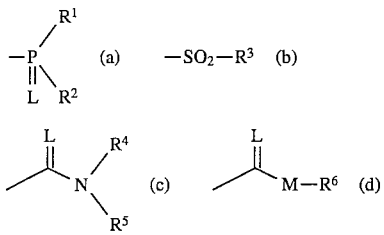

in which

L and M in each case represent oxygen or sulphur and L and M do not simultaneously represent oxygen, $R^1$, $R^2$ and $R^3$ independently of one another represent $C_1$–$C_6$-alkyl, $C_1$–$C_6$-alkoxy, $C_1$–$C_6$-alkylamino, di-($C_1$–$C_6$)-alkylamino, $C_1$–$C_6$-alkylthio, $C_3$–$C_4$-alkenylthio, $C_2$–$C_4$-alkinylthio and $C_3$–$C_6$-cycloalkylthio, each of which is optionally substituted by halogen, or represent phenyl, benzyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^4$ and $R^5$ independently of one another represent $C_1$–$C_{20}$-alkyl, $C_1$–$C_{20}$-alkoxy, $C_2$–$C_8$-alkenyl or $C_1$–$C_{20}$-alkoxy-$C_1$–$C_{20}$-alkyl, each of which is optionally substituted by halogen, or represents phenyl which is optionally substituted by halogen, $C_1$–$C_5$-halogenoalkyl, $C_1$–$C_5$-alkyl or $C_1$–$C_5$-alkoxy, or represents benzyl which is optionally substituted by halogen, $C_1$–$C_5$-alkyl, $C_1$–$C_5$-halogenoalkyl or $C_1$–$C_5$-alkoxy, $R^6$ represents $C_1$–$C_{20}$-alkyl which is optionally substituted by halogen and which can be interrupted by oxygen or represents phenyl which is optionally substituted by halogen, $C_1$–$C_5$-halogenoalkyl or $C_1$–$C_5$-alkoxy, or represents benzyl which is optionally substituted by halogen, $C_1$–$C_5$-halogenoalkyl or $C_1$–$C_5$-alkoxy, and the pure enantiomeric forms of compounds of the formula (I).

Very particularly preferred compounds of the formula (I) are those in which

X represents methyl, ethyl, propyl, i-propyl, fluorine, chlorine, bromine, methoxy and ethoxy, Y represents hydrogen, methyl, ethyl, propyl, i-propyl, butyl, i-butyl, tert.-butyl, fluorine, chlorine, bromine, methoxy, ethoxy and trifluoromethyl, Z represents methyl, ethyl, i-propyl, butyl, i-butyl, tert.-butyl, fluorine, chlorine, bromine, methoxy and ethoxy, n represents a number from 0–3, A represents hydrogen, or represents in each case straight-chain or branched $C_1$–$C_8$-alkyl, $C_3$–$C_4$-alkenyl, $C_3$–$C_4$-alkinyl, $C_1$–$C_6$-alkoxy-$C_2$–$C_4$-alkyl, $C_1$–$C_4$-polyalkoxy-$C_2$–$C_4$-alkyl and $C_1$–$C_6$-alkylthio-$C_2$–$C_4$-alkyl, each of which is optionally substituted by halogen, or represents cycloalkyl which has 3–6 ring atoms and which can be interrupted by 1–2 oxygen and/or sulphur atoms, or represents aryl, pyridine, imidazole, pyrazole, triazole, indole, thiazole or aryl-$C_1$–$C_3$-alkyl, each of which is optionally substituted by fluorine, chlorine, bromine, methyl, ethyl, propyl, iso-propyl, methoxy, ethoxy, trifluoromethyl or nitro, B represents hydrogen or in each case straight-chain or branched $C_1$–$C_8$-alkyl or $C_1$–$C_4$-alkoxyalkyl, or in which A and B together with the..carbon atom to which they are bonded form a 3- to 6-membered saturated or unsaturated ring which can be substituted by $C_1$–$C_4$-alkyl, $C_1$–$C_4$-alkoxy, trifluoromethyl, trifluoromethoxy, fluorine, chlorine and substituted phenyl and which can be interrupted by oxygen and/or sulphur, R represents the groups

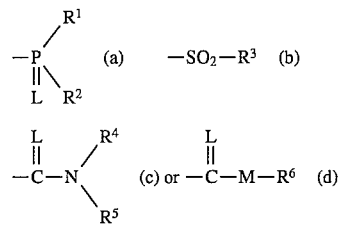

in which

L and M in each case represent oxygen or sulphur and L and M do not simultaneously represent oxygen, $R^1$, $R^2$ and $R^3$ independently of each other represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or represent phenyl, benzyl, phenoxy or phenylthio, each of which is optionally substituted by fluorine, chlorine, bromine, nitro, cyano, $C_1$–$C_2$-alkoxy, $C_1$–$C_4$-fluoroalkoxy, $C_1$–$C_2$-chloroalkoxy, $C_1$–$C_2$-alkylthio, $C_1$–$C_2$-fluoroalkylthio, $C_1$–$C_2$-chloroalkylthio or $C_1$–$C_3$-alkyl, $R^4$ and $R^5$ independently of each other represent $C_1$–$C_{10}$-alkyl, $C_1$–$C_{10}$-alkoxy or $C_1$–$C_{10}$-alkoxy-($C_1$–$C_{10}$)alkyl, each of which is optionally substituted by fluorine, chlorine or bromine, or represents phenyl which is optionally substituted by fluorine, chlorine, bromine, $C_1$–$C_{20}$-halogenoalkyl, $C_1$–$C_{20}$-alkyl or $C_1$–$C_4$-alkoxy, or represents benzyl which is optionally substituted by fluorine, chlorine, bromine, $C_1$–$C_4$-alkyl, $C_1$–$C_4$-halogenoalkyl or $C_1$–$C_4$-alkoxy, $R^6$ represents $C_1$–$C_{10}$-alkyl which is optionally substituted by fluorine, chlorine or bromine and which can be interrupted by oxygen or represents phenyl which is optionally substituted by fluorine, chlorine, bromine, $C_1$–$C_4$-halogenoalkyl or $C_1$–$C_4$-alkoxy, or represents benzyl which is optionally substituted by fluorine, chlorine, bromine, $C_1$–$C_4$-halogenoalkyl or $C_1$–$C_4$-alkoxy, and the pure enantiomeric forms of compounds of the formula (I).

The following substituted 1 H-3-aryl-pyrrolidine-2,4-dione derivatives of the general formula (I) may be mentioned individually in addition to the compounds mentioned in the Preparation Examples:

TABLE 1

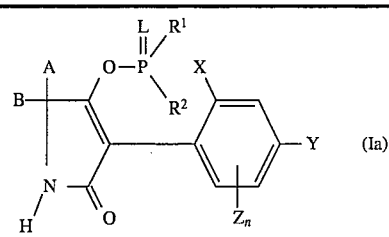

| X | Y | $Z_n$ | L | $R^1$ | $R^2$ | A | B |
|---|---|---|---|---|---|---|---|
| $CH_3$ | $CH_3$ | 6-$CH_3$ | S | $OC_2H_5$ | $nC_3H_7S$ | $CH_3$ | H |
| $CH_3$ | $CH_3$ | 6-$CH_3$ | O | $N(CH_3)_2$ | $N(CH_3)_2$ | $CH_3$ | H |
| $CH_3$ | $CH_3$ | 6-$CH_3$ | S | $CH_3$ | $SCH_2-CH(CH_3)_2$ | $CH_3$ | H |
| $CH_3$ | $CH_3$ | 6-$CH_3$ | S | $CH_3$ | $OCH_3$ | $CH_3$ | H |
| $CH_3$ | $CH_3$ | 6-$CH_3$ | S | $CH_3$ | $OC_2H_5$ | $CH_3$ | H |
| $CH_3$ | $CH_3$ | 6-$CH_3$ | S | $CH_3$ | $OC_3H_7$-i | $CH_3$ | H |
| $CH_3$ | $CH_3$ | 6-$CH_3$ | S | $CH_3$ | $OC_4H_9$-sec | $CH_3$ | H |
| $CH_3$ | $CH_3$ | 6-$CH_3$ | S | $CH_3$ | $OC_4H_9$-iso | $CH_3$ | H |
| $CH_3$ | $CH_3$ | 6-$CH_3$ | S | $C_2H_5$ | $OCH_3$ | $CH_3$ | H |
| $CH_3$ | $CH_3$ | 6-$CH_3$ | S | $C_2H_5$ | $OC_3H_7$-i | $CH_3$ | H |
| $CH_3$ | $CH_3$ | 6-$CH_3$ | S | $C_2H_5$ | $OC_4H_9$-sec | $CH_3$ | H |
| $CH_3$ | $CH_3$ | 6-$CH_3$ | S | $C_2H_5$ | $OC_3H_7$-i | $CH_3$ | H |
| $CH_3$ | $CH_3$ | 6-$CH_3$ | S | $OC_2H_5$ | $nC_3H_7S$ | $CH_3$ | $CH_3$ |
| $CH_3$ | $CH_3$ | 6-$CH_3$ | O | $N(CH_3)_2$ | $N(CH_3)_2$ | $CH_3$ | $CH_3$ |
| $CH_3$ | $CH_3$ | 6-$CH_3$ | S | $CH_3$ | $OCH_3$ | $CH_3$ | $CH_3$ |
| $CH_3$ | $CH_3$ | 6-$CH_3$ | S | $CH_3$ | $OC_2H_5$ | $CH_3$ | $CH_3$ |
| $CH_3$ | $CH_3$ | 6-$CH_3$ | S | $CH_3$ | $OC_3H_7$-i | $CH_3$ | $CH_3$ |
| $CH_3$ | $CH_3$ | 6-$CH_3$ | S | $CH_3$ | $OC_4H_9$-sec | $CH_3$ | $CH_3$ |
| $CH_3$ | $CH_3$ | 6-$CH_3$ | S | $CH_3$ | $OC_4H_9$-iso | $CH_3$ | $CH_3$ |
| $CH_3$ | $CH_3$ | 6-$CH_3$ | S | $C_2H_5$ | $OCH_3$ | $CH_3$ | $CH_3$ |
| $CH_3$ | $CH_3$ | 6-$CH_3$ | S | $C_2H_5$ | $OC_3H_7$-i | $CH_3$ | $CH_3$ |
| $CH_3$ | $CH_3$ | 6-$CH_3$ | S | $C_2H_5$ | $OC_4H_9$-sec | $CH_3$ | $CH_3$ |
| $CH_3$ | $CH_3$ | 6-$CH_3$ | S | $C_2H_5$ | $OC_3H_7$-i | $CH_3$ | $CH_3$ |
| $CH_3$ | $CH_3$ | 6-$CH_3$ | S | $OC_2H_5$ | $nC_3H_7S$ | $-(CH_2)_5-$ | |
| $CH_3$ | $CH_3$ | 6-$CH_3$ | O | $N(CH_3)_2$ | $N(CH_3)_2$ | $-(CH_2)_5-$ | |
| $CH_3$ | $CH_3$ | 6-$CH_3$ | S | $CH_3$ | $SCH_2-CH(CH_3)_2$ | $-(CH_2)_5-$ | |
| $CH_3$ | $CH_3$ | 6-$CH_3$ | S | $CH_3$ | $OCH_3$ | $-(CH_2)_5-$ | |
| $CH_3$ | $CH_3$ | 6-$CH_3$ | S | $CH_3$ | $OC_2H_5$ | $-(CH_2)_5-$ | |
| $CH_3$ | $CH_3$ | 6-$CH_3$ | S | $CH_3$ | $OC_3H_7$-i | $-(CH_2)_5-$ | |
| $CH_3$ | $CH_3$ | 6-$CH_3$ | S | $CH_3$ | $OC_4H_9$-sec | $-(CH_2)_5-$ | |
| $CH_3$ | $CH_3$ | 6-$CH_3$ | S | $CH_3$ | $OC_4H_9$-iso | $-(CH_2)_5-$ | |
| $CH_3$ | $CH_3$ | 6-$CH_3$ | S | $C_2H_5$ | $OCH_3$ | $-(CH_2)_5-$ | |
| $CH_3$ | $CH_3$ | 6-$CH_3$ | S | $C_2H_5$ | $OC_3H_7$-i | $-(CH_2)_5-$ | |
| $CH_3$ | $CH_3$ | 6-$CH_3$ | S | $C_2H_5$ | $OC_4H_9$-sec | $-(CH_2)_5-$ | |
| $CH_3$ | $CH_3$ | 6-$CH_3$ | S | $C_2H_5$ | $OC_3H_7$-i | $-(CH_2)_5-$ | |
| $CH_3$ | $CH_3$ | 6-$CH_3$ | S | $OC_2H_5$ | $OC_2H_5$ | $CH_3$ | H |
| $CH_3$ | $CH_3$ | 6-$CH_3$ | S | $C_2H_5$ | $OC_2H_5$ | $CH_3$ | H |
| $CH_3$ | $CH_3$ | 6-$CH_3$ | S | $OC_2H_5$ | $OC_2H_5$ | $CH_3$ | H |
| $CH_3$ | $CH_3$ | 6-$CH_3$ | O | $OC_2H_5$ | $SC_3H_7$-i | $CH_3$ | H |
| $CH_3$ | $CH_3$ | 6-$CH_3$ | S | $OCH_3$ | $N(CH_3)_2$ | $CH_3$ | H |
| $CH_3$ | $CH_3$ | 6-$CH_3$ | S | $CH_3$ | $SCH(CH_3)C_2H_5$ | $CH_3$ | H |
| $CH_3$ | $CH_3$ | 6-$CH_3$ | O | $C_2H_5O$ | $SCH(CH_3)C_2H_5$ | $CH_3$ | H |
| $CH_3$ | $CH_3$ | 6-$CH_3$ | S | $OC_2H_5$ | $OC_2H_5$ | $CH_3$ | $CH_3$ |
| $CH_3$ | $CH_3$ | 6-$CH_3$ | S | $C_2H_5$ | $OC_2H_5$ | $CH_3$ | $CH_3$ |
| $CH_3$ | $CH_3$ | 6-$CH_3$ | S | $OC_2H_5$ | $OC_2H_5$ | $CH_3$ | $CH_3$ |
| $CH_3$ | $CH_3$ | 6-$CH_3$ | O | $OC_2H_5$ | $SC_3H_7$-i | $CH_3$ | $CH_3$ |
| $CH_3$ | $CH_3$ | 6-$CH_3$ | S | $OCH_3$ | $N(CH_3)_2$ | $CH_3$ | $CH_3$ |
| $CH_3$ | $CH_3$ | 6-$CH_3$ | S | $CH_3$ | $SCH(CH_3)C_2H_5$ | $CH_3$ | $CH_3$ |
| $CH_3$ | $CH_3$ | 6-$CH_3$ | O | $C_2H_5O$ | $SCH(CH_3)C_2H_5$ | $CH_3$ | $CH_3$ |
| $CH_3$ | $CH_3$ | 6-$CH_3$ | S | $OC_2H_5$ | $OC_2H_5$ | $-(CH_2)_5-$ | |
| $CH_3$ | $CH_3$ | 6-$CH_3$ | S | $C_2H_5$ | $OC_2H_5$ | $-(CH_2)_5-$ | |
| $CH_3$ | $CH_3$ | 6-$CH_3$ | S | $OC_2H_5$ | $OC_2H_5$ | $-(CH_2)_5-$ | |
| $CH_3$ | $CH_3$ | 6-$CH_3$ | O | $OC_2H_5$ | $SC_3H_7$-i | $-(CH_2)_5-$ | |
| $CH_3$ | $CH_3$ | 6-$CH_3$ | S | $OCH_3$ | $N(CH_3)_2$ | $-(CH_2)_5-$ | |
| $CH_3$ | $CH_3$ | 6-$CH_3$ | S | $CH_3$ | $SCH(CH_3)C_2H_5$ | $-(CH_2)_5-$ | |
| $CH_3$ | $CH_3$ | 6-$CH_3$ | O | $C_2H_5O$ | $SCH(CH_3)C_2H_5$ | $-(CH_2)_5-$ | |
| $CH_3$ | $CH_3$ | 6-$CH_3$ | O | $CH_3O$ | $SC_3H_7$-i | $CH_3$ | H |
| $CH_3$ | $CH_3$ | 6-$CH_3$ | O | n-$C_4H_9O$ | $SC_3H_7$-i | $CH_3$ | H |
| $CH_3$ | $CH_3$ | 6-$CH_3$ | O | $CH_3O$ | $SC_4H_9$-sek | $CH_3$ | H |
| $CH_3$ | $CH_3$ | 6-$CH_3$ | O | n-$C_4H_9$ | $SC_4H_9$-sek | $CH_3$ | H |
| $CH_3$ | $CH_3$ | 6-$CH_3$ | O | $CH_3O$ | $SC_3H_7$-i | $CH_3$ | $CH_3$ |
| $CH_3$ | $CH_3$ | 6-$CH_3$ | O | n-$C_4H_9O$ | $SC_3H_7$-i | $CH_3$ | $CH_3$ |
| $CH_3$ | $CH_3$ | 6-$CH_3$ | O | $CH_3O$ | $SC_4H_9$-sek | $CH_3$ | $CH_3$ |
| $CH_3$ | $CH_3$ | 6-$CH_3$ | O | n-$C_4H_9$ | $SC_4H_9$-sek | $CH_3$ | $CH_3$ |
| $CH_3$ | $CH_3$ | 6-$CH_3$ | O | $CH_3O$ | $SC_3H_7$-i | $-(CH_2)_5-$ | |
| $CH_3$ | $CH_3$ | 6-$CH_3$ | O | n-$C_4H_9O$ | $SC_3H_7$-i | $-(CH_2)_5-$ | |

TABLE 1-continued

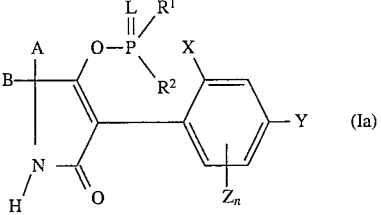

(Ia)

| X | Y | $Z_n$ | L | $R^1$ | $R^2$ | A | B |
|---|---|---|---|---|---|---|---|
| $CH_3$ | $CH_3$ | 6-$CH_3$ | O | $CH_3O$ | $SC_4H_9$-sek | $-(CH_2)_5-$ | |
| $CH_3$ | $CH_3$ | 6-$CH_3$ | O | n-$C_4H_9$ | $SC_4H_9$-sek | $-(CH_2)_5-$ | |

TABLE 2

(Ib)

| X | Y | $Z_n$ | $R^3$ | A | B |
|---|---|---|---|---|---|
| $CH_3$ | $CH_3$ | 6-$CH_3$ | $CH_3$ | $CH_3$ | H |
| $CH_3$ | $CH_3$ | 6-$CH_3$ | $C_4F_9$ | $CH_3$ | H |
| $CH_3$ | $CH_3$ | 6-$CH_3$ | $C_4F_9$ | $CH_3$ | H |
| $CH_3$ | $CH_3$ | 6-$CH_3$ | phenyl | $CH_3$ | H |
| $CH_3$ | $CH_3$ | 6-$CH_3$ | 4-$CH_3$-phenyl | $CH_3$ | H |
| $CH_3$ | $CH_3$ | 6-$CH_3$ | 4-Cl-phenyl | $CH_3$ | H |
| $CH_3$ | $CH_3$ | 6-$CH_3$ | benzyl | $CH_3$ | H |
| $CH_3$ | $CH_3$ | 6-$CH_3$ | 4-Cl-benzyl | $CH_3$ | H |
| $CH_3$ | $CH_3$ | 6-$CH_3$ | $CH_3$ | $CH_3$ | $CH_3$ |
| $CH_3$ | $CH_3$ | 6-$CH_3$ | $C_4F_9$ | $CH_3$ | $CH_3$ |
| $CH_3$ | $CH_3$ | 6-$CH_3$ | $C_4F_9$ | $CH_3$ | $CH_3$ |
| $CH_3$ | $CH_3$ | 6-$CH_3$ | phenyl | $CH_3$ | $CH_3$ |
| $CH_3$ | $CH_3$ | 6-$CH_3$ | 4-$CH_3$-phenyl | $CH_3$ | $CH_3$ |
| $CH_3$ | $CH_3$ | 6-$CH_3$ | 4-Cl-phenyl | $CH_3$ | $CH_3$ |
| $CH_3$ | $CH_3$ | 6-$CH_3$ | benzyl | $CH_3$ | $CH_3$ |
| $CH_3$ | $CH_3$ | 6-$CH_3$ | 4-Cl-benzyl | $CH_3$ | $CH_3$ |
| $CH_3$ | $CH_3$ | 6-$CH_3$ | $CH_3$ | $-(CH_2)_5-$ | |
| $CH_3$ | $CH_3$ | 6-$CH_3$ | $C_4F_9$ | $-(CH_2)_5-$ | |
| $CH_3$ | $CH_3$ | 6-$CH_3$ | $C_4F_9$ | $-(CH_2)_5-$ | |
| $CH_3$ | $CH_3$ | 6-$CH_3$ | phenyl | $-(CH_2)_5-$ | |
| $CH_3$ | $CH_3$ | 6-$CH_3$ | 4-$CH_3$-phenyl | $-(CH_2)_5-$ | |
| $CH_3$ | $CH_3$ | 6-$CH_3$ | 4-Cl-phenyl | $-(CH_2)_5-$ | |
| $CH_3$ | $CH_3$ | 6-$CH_3$ | benzyl | $-(CH_2)_5-$ | |
| $CH_3$ | $CH_3$ | 6-$CH_3$ | 4-Cl-benzyl | $-(CH_2)_5-$ | |

TABLE 3

(Structure Ic: a cyclic compound with O-C(=L)-N(R⁴)(R⁵) group, A, B substituents, and phenyl ring with X, Y, Zₙ substituents)

| X | Y | Zₙ | L | R⁴ | R⁵ | A | B |
|---|---|---|---|---|---|---|---|
| CH₃ | CH₃ | 6-CH₃ | S | CH₃ | CH₃ | CH₃ | H |
| CH₃ | CH₃ | 6-CH₃ | O | CH₃ | CH₃ | CH₃ | H |
| CH₃ | CH₃ | 6-CH₃ | S | C₂H₅ | C₂H₅ | CH₃ | H |
| CH₃ | CH₃ | 6-CH₃ | O | C₂H₅ | C₂H₅ | CH₃ | H |
| CH₃ | CH₃ | 6-CH₃ | S | C₃H₇(n) | C₃H₇(n) | CH₃ | H |
| CH₃ | CH₃ | 6-CH₃ | O | —CH₂—CH=CH₂ | —CH₂—CH=CH₂ | CH₃ | H |
| CH₃ | CH₃ | 6-CH₃ | O | CH₃ | phenyl | CH₃ | H |
| CH₃ | CH₃ | 6-CH₃ | O | C₃H₇(n) | C₃H₇(n) | CH₃ | H |
| CH₃ | CH₃ | 6-CH₃ | O | —(CH₂)₅— | | CH₃ | H |
| CH₃ | CH₃ | 6-CH₃ | S | —(CH₂)₂—O—(CH₂)₂— | | CH₃ | H |
| CH₃ | CH₃ | 6-CH₃ | S | CH₃ | CH₃ | CH₃ | CH₃ |
| CH₃ | CH₃ | 6-CH₃ | O | CH₃ | CH₃ | CH₃ | CH₃ |
| CH₃ | CH₃ | 6-CH₃ | S | C₂H₅ | C₂H₅ | CH₃ | CH₃ |
| CH₃ | CH₃ | 6-CH₃ | O | C₂H₅ | C₂H₅ | CH₃ | CH₃ |
| CH₃ | CH₃ | 6-CH₃ | S | C₃H₇(n) | C₃H₇(n) | CH₃ | CH₃ |
| CH₃ | CH₃ | 6-CH₃ | O | —CH₂—CH=CH₂ | —CH₂—CH=CH₂ | CH₃ | CH₃ |
| CH₃ | CH₃ | 6-CH₃ | O | CH₃ | phenyl | CH₃ | CH₃ |
| CH₃ | CH₃ | 6-CH₃ | O | C₃H₇(n) | C₃H₇(n) | CH₃ | CH₃ |
| CH₃ | CH₃ | 6-CH₃ | O | —(CH₂)₅— | | CH₃ | CH₃ |
| CH₃ | CH₃ | 6-CH₃ | S | —(CH₂)₂—O—(CH₂)₂— | | CH₃ | CH₃ |
| CH₃ | CH₃ | 6-CH₃ | S | CH₃ | CH₃ | —(CH₂)₅— | |
| CH₃ | CH₃ | 6-CH₃ | O | CH₃ | CH₃ | —(CH₂)₅— | |
| CH₃ | CH₃ | 6-CH₃ | S | C₂H₅ | C₂H₅ | —(CH₂)₅— | |
| CH₃ | CH₃ | 6-CH₃ | O | C₂H₅ | C₂H₅ | —(CH₂)₅— | |
| CH₃ | CH₃ | 6-CH₃ | S | C₃H₇(n) | C₃H₇(n) | —(CH₂)₅— | |
| CH₃ | CH₃ | 6-CH₃ | O | —CH₂—CH=CH₂ | —CH₂—CH=CH₂ | —(CH₂)₅— | |
| CH₃ | CH₃ | 6-CH₃ | O | CH₃ | phenyl | —(CH₂)₅— | |
| CH₃ | CH₃ | 6-CH₃ | O | C₃H₇(n) | C₃H₇(n) | —(CH₂)₅— | |
| CH₃ | CH₃ | 6-CH₃ | O | —(CH₂)₅— | | —(CH₂)₅— | |
| CH₃ | CH₃ | 6-CH₃ | S | —(CH₂)₂—O—(CH₂)₂— | | —(CH₂)₅— | |

TABLE 4

(Structure Id: similar cyclic compound with O-C(=L)-M-R⁶ group)

| X | Y | Zₙ | L | M | R⁶ | A | B |
|---|---|---|---|---|---|---|---|
| Cl | Cl | H | O | S | CH₃ | CH₃ | H |
| Cl | Cl | H | O | S | C₂H₅ | CH₃ | H |
| Cl | Cl | H | O | S | C₃H₇ | CH₃ | H |
| Cl | Cl | H | O | S | i-C₃H₇ | CH₃ | H |

TABLE 4-continued

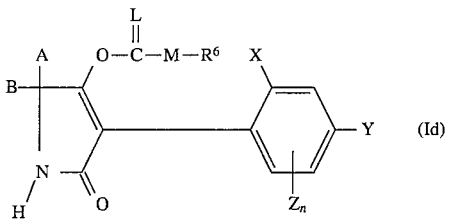

(Id)

| X | Y | Z_n | L | M | R^6 | A | B |
|---|---|---|---|---|---|---|---|
| Cl | Cl | H | O | S | i-C_4H_9 | CH_3 | H |
| Cl | Cl | H | O | S | s-C_4H_9 | CH_3 | H |
| Cl | Cl | H | O | S | t-C_4H_9 | CH_3 | H |
| Cl | Cl | H | O | S | —CH_2—C(CH_3)_3 | CH_3 | H |
| Cl | Cl | H | O | S | —(CH_2)_2—C(CH_3)_3 | CH_3 | H |
| Cl | Cl | H | O | S | —CH_2—CH=CH_2 | CH_3 | H |
| Cl | Cl | H | O | S | —CH_2—C≡CH | CH_3 | H |
| Cl | Cl | H | O | S | —CH_2—C_6H_5 | CH_3 | H |
| Cl | Cl | H | O | S | CH_3 | CH_3 | CH_3 |
| Cl | Cl | H | O | S | C_2H_5 | CH_3 | CH_3 |
| Cl | Cl | H | O | S | C_3H_7 | CH_3 | CH_3 |
| Cl | Cl | H | O | S | i-C_3H_7 | CH_3 | CH_3 |
| Cl | Cl | H | O | S | i-C_4H_9 | CH_3 | CH_3 |
| Cl | Cl | H | O | S | s-C_4H_9 | CH_3 | CH_3 |
| Cl | Cl | H | O | S | t-C_4H_9 | CH_3 | CH_3 |
| Cl | Cl | H | O | S | —CH_2—C(CH_3)_3 | CH_3 | CH_3 |
| Cl | Cl | H | O | S | —(CH_2)_2—C(CH_3)_3 | CH_3 | CH_3 |
| Cl | Cl | H | O | S | —CH_2—CH=CH_2 | CH_3 | CH_3 |
| Cl | Cl | H | O | S | —CH_2—C≡CH | CH_3 | CH_3 |
| Cl | Cl | H | O | S | —CH_2—C_6H_5 | CH_3 | CH_3 |
| Cl | Cl | H | O | S | CH_3 | —(CH_2)_5— | |
| Cl | Cl | H | O | S | C_2H_5 | —(CH_2)_5— | |
| Cl | Cl | H | O | S | C_3H_7 | —(CH_2)_5— | |
| Cl | Cl | H | O | S | i-C_3H_7 | —(CH_2)_5— | |
| Cl | Cl | H | O | S | i-C_4H_9 | —(CH_2)_5— | |
| Cl | Cl | H | O | S | s-C_4H_9 | —(CH_2)_5— | |
| Cl | Cl | H | O | S | t-C_4H_9 | —(CH_2)_5— | |
| Cl | Cl | H | O | S | —CH_2—C(CH_3)_3 | —(CH_2)_5— | |
| Cl | Cl | H | O | S | —(CH_2)_2—C(CH_3)_3 | —(CH_2)_5— | |
| Cl | Cl | H | O | S | —CH_2—CH=CH_2 | —(CH_2)_5— | |
| Cl | Cl | H | O | S | —CH_2—C≡CH | —(CH_2)_5— | |
| Cl | Cl | H | O | S | —CH_2—C_6H_5 | —(CH_2)_5— | |
| CH_3 | CH_3 | H | O | S | CH_3 | CH_3 | H |
| CH_3 | CH_3 | H | O | S | C_2H_5 | CH_3 | H |
| CH_3 | CH_3 | H | O | S | C_3H_7 | CH_3 | H |
| CH_3 | CH_3 | H | O | S | i-C_3H_7 | CH_3 | H |
| CH_3 | CH_3 | H | O | S | i-C_4H_9 | CH_3 | H |
| CH_3 | CH_3 | H | O | S | s-C_4H_9 | CH_3 | H |
| CH_3 | CH_3 | H | O | S | t-C_4H_9 | CH_3 | H |
| CH_3 | CH_3 | H | O | S | —CH_2—C(CH_3)_3 | CH_3 | H |
| CH_3 | CH_3 | H | O | S | —(CH_2)_2—C(CH_3)_3 | CH_3 | H |
| CH_3 | CH_3 | H | O | S | —CH_2—CH=CH_2 | CH_3 | H |
| CH_3 | CH_3 | H | O | S | —CH_2—C≡CH | CH_3 | H |
| CH_3 | CH_3 | H | O | S | —CH_2—C_6H_5 | CH_3 | H |
| CH_3 | CH_3 | H | O | S | CH_3 | CH_3 | CH_3 |
| CH_3 | CH_3 | H | O | S | C_2H_5 | CH_3 | CH_3 |
| CH_3 | CH_3 | H | O | S | C_3H_7 | CH_3 | CH_3 |
| CH_3 | CH_3 | H | O | S | i-C_3H_7 | CH_3 | CH_3 |
| CH_3 | CH_3 | H | O | S | i-C_4H_9 | CH_3 | CH_3 |
| CH_3 | CH_3 | H | O | S | s-C_4H_9 | CH_3 | CH_3 |
| CH_3 | CH_3 | H | O | S | t-C_4H_9 | CH_3 | CH_3 |
| CH_3 | CH_3 | H | O | S | —CH_2—C(CH_3)_3 | CH_3 | CH_3 |
| CH_3 | CH_3 | H | O | S | —(CH_2)_2—C(CH_3)_3 | CH_3 | CH_3 |
| CH_3 | CH_3 | H | O | S | —CH_2—CH=CH_2 | CH_3 | CH_3 |
| CH_3 | CH_3 | H | O | S | —CH_2—C≡CH | CH_3 | CH_3 |
| CH_3 | CH_3 | H | O | S | —CH_2—C_6H_5 | CH_3 | CH_3 |
| CH_3 | CH_3 | H | O | S | CH_3 | —(CH_2)_5— | |
| CH_3 | CH_3 | H | O | S | C_2H_5 | —(CH_2)_5— | |
| CH_3 | CH_3 | H | O | S | C_3H_7 | —(CH_2)_5— | |
| CH_3 | CH_3 | H | O | S | i-C_3H_7 | —(CH_2)_5— | |
| CH_3 | CH_3 | H | O | S | i-C_4H_9 | —(CH_2)_5— | |
| CH_3 | CH_3 | H | O | S | s-C_4H_9 | —(CH_2)_5— | |
| CH_3 | CH_3 | H | O | S | t-C_4H_9 | —(CH_2)_5— | |
| CH_3 | CH_3 | H | O | S | —CH_2—C(CH_3)_3 | —(CH_2)_5— | |
| CH_3 | CH_3 | H | O | S | —(CH_2)_2—C(CH_3)_3 | —(CH_2)_5— | |
| CH_3 | CH_3 | H | O | S | —CH_2—CH=CH_2 | —(CH_2)_5— | |
| CH_3 | CH_3 | H | O | S | —CH_2—C≡CH | —(CH_2)_5— | |
| CH_3 | CH_3 | H | O | S | —CH_2—C_6H_5 | —(CH_2)_5— | |
| CH_3 | CH_3 | 6-CH_3 | O | S | CH_3 | CH_3 | H |
| CH_3 | CH_3 | 6-CH_3 | O | S | C_2H_5 | CH_3 | H |
| CH_3 | CH_3 | 6-CH_3 | O | S | C_3H_7 | CH_3 | H |
| CH_3 | CH_3 | 6-CH_3 | O | S | i-C_3H_7 | CH_3 | H |
| CH_3 | CH_3 | 6-CH_3 | O | S | i-C_4H_9 | CH_3 | H |
| CH_3 | CH_3 | 6-CH_3 | O | S | s-C_4H_9 | CH_3 | H |
| CH_3 | CH_3 | 6-CH_3 | O | S | t-C_4H_9 | CH_3 | H |
| CH_3 | CH_3 | 6-CH_3 | O | S | —CH_2—CH=CH_2 | CH_3 | H |
| CH_3 | CH_3 | 6-CH_3 | O | S | —CH_2—C≡CH | CH_3 | H |
| CH_3 | CH_3 | 6-CH_3 | O | S | —CH_2—C_6H_5 | CH_3 | H |
| CH_3 | CH_3 | 6-CH_3 | O | S | CH_3 | CH_3 | CH_3 |
| CH_3 | CH_3 | 6-CH_3 | O | S | C_2H_5 | CH_3 | CH_3 |
| CH_3 | CH_3 | 6-CH_3 | O | S | C_3H_7 | CH_3 | CH_3 |
| CH_3 | CH_3 | 6-CH_3 | O | S | i-C_3H_7 | CH_3 | CH_3 |
| CH_3 | CH_3 | 6-CH_3 | O | S | i-C_4H_9 | CH_3 | CH_3 |

TABLE 4-continued

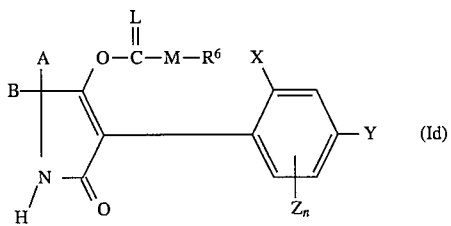

(Id)

| X | Y | $Z_n$ | L | M | $R^6$ | A | B |
|---|---|---|---|---|---|---|---|
| $CH_3$ | $CH_3$ | 6-$CH_3$ | O | S | s-$C_4H_9$ | $CH_3$ | $CH_3$ |
| $CH_3$ | $CH_3$ | 6-$CH_3$ | O | S | t-$C_4H_9$ | $CH_3$ | $CH_3$ |
| $CH_3$ | $CH_3$ | 6-$CH_3$ | O | S | $-CH_2-C(CH_3)_3$ | $CH_3$ | $CH_3$ |
| $CH_3$ | $CH_3$ | 6-$CH_3$ | O | S | $-(CH_2)_2-C(CH_3)_3$ | $CH_3$ | $CH_3$ |
| $CH_3$ | $CH_3$ | 6-$CH_3$ | O | S | $-CH_2-CH=CH_2$ | $CH_3$ | $CH_3$ |
| $CH_3$ | $CH_3$ | 6-$CH_3$ | O | S | $-CH_2-C\equiv CH$ | $CH_3$ | $CH_3$ |
| $CH_3$ | $CH_3$ | 6-$CH_3$ | O | S | $-CH_2-C_6H_5$ | $CH_3$ | $CH_3$ |
| $CH_3$ | $CH_3$ | 6-$CH_3$ | O | S | $CH_3$ | $-(CH_2)_5-$ | |
| $CH_3$ | $CH_3$ | 6-$CH_3$ | O | S | $C_2H_5$ | $-(CH_2)_5-$ | |
| $CH_3$ | $CH_3$ | 6-$CH_3$ | O | S | $C_3H_7$ | $-(CH_2)_5-$ | |
| $CH_3$ | $CH_3$ | 6-$CH_3$ | O | S | i-$C_3H_7$ | $-(CH_2)_5-$ | |
| $CH_3$ | $CH_3$ | 6-$CH_3$ | O | S | i-$C_4H_9$ | $-(CH_2)_5-$ | |
| $CH_3$ | $CH_3$ | 6-$CH_3$ | O | S | s-$C_4H_9$ | $-(CH_2)_5-$ | |
| $CH_3$ | $CH_3$ | 6-$CH_3$ | O | S | t-$C_4H_9$ | $-(CH_2)_5-$ | |
| $CH_3$ | $CH_3$ | 6-$CH_3$ | O | S | $-CH_2-C(CH_3)_3$ | $-(CH_2)_5-$ | |
| $CH_3$ | $CH_3$ | 6-$CH_3$ | O | S | $-(CH_2)_2-C(CH_3)_3$ | $-(CH_2)_5-$ | |
| $CH_3$ | $CH_3$ | 6-$CH_3$ | O | S | $-CH_2-CH=CH_2$ | $-(CH_2)_5-$ | |
| $CH_3$ | $CH_3$ | 6-$CH_3$ | O | S | $-CH_2-C\equiv CH$ | $-(CH_2)_5-$ | |
| $CH_3$ | $CH_3$ | 6-$CH_3$ | O | S | $-CH_2-C_6H_5$ | $-(CH_2)_5-$ | |
| Cl | Cl | H | S | S | $CH_3$ | $CH_3$ | H |
| Cl | Cl | H | S | S | $C_2H_5$ | $CH_3$ | H |
| Cl | Cl | H | S | S | $C_3H_7$ | $CH_3$ | H |
| Cl | Cl | H | S | S | i-$C_3H_7$ | $CH_3$ | H |
| Cl | Cl | H | S | S | i-$C_4H_9$ | $CH_3$ | H |
| Cl | Cl | H | S | S | s-$C_4H_9$ | $CH_3$ | H |
| Cl | Cl | H | S | S | $-CH_2-C(CH_3)_3$ | $CH_3$ | H |
| Cl | Cl | H | S | S | $-(CH_2)_2-C(CH_3)_3$ | $CH_3$ | H |
| Cl | Cl | H | S | S | $-CH_2-CH=CH_2$ | $CH_3$ | H |
| Cl | Cl | H | S | S | $-CH_2-C\equiv CH$ | $CH_3$ | H |
| Cl | Cl | H | S | S | $-CH_2-C_6H_5$ | $CH_3$ | H |
| Cl | Cl | H | S | S | $CH_3$ | $CH_3$ | $CH_3$ |
| Cl | Cl | H | S | S | $C_2H_5$ | $CH_3$ | $CH_3$ |
| Cl | Cl | H | S | S | $C_3H_7$ | $CH_3$ | $CH_3$ |
| Cl | Cl | H | S | S | i-$C_3H_7$ | $CH_3$ | $CH_3$ |
| Cl | Cl | H | S | S | i-$C_4H_9$ | $CH_3$ | $CH_3$ |
| Cl | Cl | H | S | S | s-$C_4H_9$ | $CH_3$ | $CH_3$ |
| Cl | Cl | H | S | S | $-CH_2-C(CH_3)_3$ | $CH_3$ | $CH_3$ |
| Cl | Cl | H | S | S | $-(CH_2)_2-C(CH_3)_3$ | $CH_3$ | $CH_3$ |
| Cl | Cl | H | S | S | $-CH_2-CH=CH_2$ | $CH_3$ | $CH_3$ |
| Cl | Cl | H | S | S | $-CH_2-C\equiv CH$ | $CH_3$ | $CH_3$ |
| Cl | Cl | H | S | S | $-CH_2-C_6H_5$ | $CH_3$ | $CH_3$ |
| Cl | Cl | H | S | S | $CH_3$ | $-(CH_2)_5-$ | |
| Cl | Cl | H | S | S | $C_2H_5$ | $-(CH_2)_5-$ | |
| Cl | Cl | H | S | S | $C_3H_7$ | $-(CH_2)_5-$ | |
| Cl | Cl | H | S | S | i-$C_3H_7$ | $-(CH_2)_5-$ | |
| Cl | Cl | H | S | S | i-$C_4H_9$ | $-(CH_2)_5-$ | |
| Cl | Cl | H | S | S | s-$C_4H_9$ | $-(CH_2)_5-$ | |
| Cl | Cl | H | S | S | $-CH_2-C(CH_3)_3$ | $-(CH_2)_5-$ | |
| Cl | Cl | H | S | S | $-(CH_2)_2-C(CH_3)_3$ | $-(CH_2)_5-$ | |
| Cl | Cl | H | S | S | $-CH_2-CH=CH_2$ | $-(CH_2)_5-$ | |
| Cl | Cl | H | S | S | $-CH_2-C\equiv CH$ | $-(CH_2)_5-$ | |
| Cl | Cl | H | S | S | $-CH_2-C_6H_5$ | $-(CH_2)_5-$ | |
| $CH_3$ | $CH_3$ | H | S | S | $CH_3$ | $CH_3$ | H |
| $CH_3$ | $CH_3$ | H | S | S | $C_2H_5$ | $CH_3$ | H |
| $CH_3$ | $CH_3$ | H | S | S | $C_3H_7$ | $CH_3$ | H |
| $CH_3$ | $CH_3$ | H | S | S | i-$C_3H_7$ | $CH_3$ | H |
| $CH_3$ | $CH_3$ | H | S | S | i-$C_4H_9$ | $CH_3$ | H |
| $CH_3$ | $CH_3$ | H | S | S | s-$C_4H_9$ | $CH_3$ | H |
| $CH_3$ | $CH_3$ | H | S | S | $-CH_2-C(CH_3)_3$ | $CH_3$ | H |
| $CH_3$ | $CH_3$ | H | S | S | $-(CH_2)_2-C(CH_3)_3$ | $CH_3$ | H |
| $CH_3$ | $CH_3$ | H | S | S | $-CH_2-CH=CH_2$ | $CH_3$ | H |
| $CH_3$ | $CH_3$ | H | S | S | $-CH_2-C\equiv CH$ | $CH_3$ | H |
| $CH_3$ | $CH_3$ | H | S | S | $-CH_2-C_6H_5$ | $CH_3$ | H |
| $CH_3$ | $CH_3$ | H | S | S | $CH_3$ | $CH_3$ | $CH_3$ |
| $CH_3$ | $CH_3$ | H | S | S | $C_2H_5$ | $CH_3$ | $CH_3$ |
| $CH_3$ | $CH_3$ | H | S | S | $C_3H_7$ | $CH_3$ | $CH_3$ |
| $CH_3$ | $CH_3$ | H | S | S | i-$C_3H_7$ | $CH_3$ | $CH_3$ |
| $CH_3$ | $CH_3$ | H | S | S | i-$C_4H_9$ | $CH_3$ | $CH_3$ |
| $CH_3$ | $CH_3$ | H | S | S | s-$C_4H_9$ | $CH_3$ | $CH_3$ |
| $CH_3$ | $CH_3$ | H | S | S | $-CH_2-C(CH_3)_3$ | $CH_3$ | $CH_3$ |
| $CH_3$ | $CH_3$ | H | S | S | $-(CH_2)_2-C(CH_3)_3$ | $CH_3$ | $CH_3$ |
| $CH_3$ | $CH_3$ | H | S | S | $-CH_2-CH=CH_2$ | $CH_3$ | $CH_3$ |
| $CH_3$ | $CH_3$ | H | S | S | $-CH_2-C\equiv CH$ | $CH_3$ | $CH_3$ |
| $CH_3$ | $CH_3$ | H | S | S | $-CH_2-C_6H_5$ | $CH_3$ | $CH_3$ |
| $CH_3$ | $CH_3$ | H | S | S | $CH_3$ | $-(CH_2)_5-$ | |
| $CH_3$ | $CH_3$ | H | S | S | $C_2H_5$ | $-(CH_2)_5-$ | |
| $CH_3$ | $CH_3$ | H | S | S | $C_3H_7$ | $-(CH_2)_5-$ | |
| $CH_3$ | $CH_3$ | H | S | S | i-$C_3H_7$ | $-(CH_2)_5-$ | |
| $CH_3$ | $CH_3$ | H | S | S | i-$C_4H_9$ | $-(CH_2)_5-$ | |
| $CH_3$ | $CH_3$ | H | S | S | s-$C_4H_9$ | $-(CH_2)_5-$ | |
| $CH_3$ | $CH_3$ | H | S | S | $-CH_2-C(CH_3)_3$ | $-(CH_2)_5-$ | |

TABLE 4-continued $$\begin{array}{c}\overset{L}{\underset{\|}{O-C-M-R^6}} \\ \overset{A}{\underset{B}{\diagup}} \overset{\diagdown}{\phantom{X}} \end{array}$$ (Id)

(structure with phenyl bearing X, Y, $Z_n$ substituents and pyrrolidine-dione NH)

| X | Y | $Z_n$ | L | M | $R^6$ | A | B |
|---|---|---|---|---|---|---|---|
| CH₃ | CH₃ | H | S | S | –(CH₂)₂–C(CH₃)₃ | –(CH₂)₅– | |
| CH₃ | CH₃ | H | S | S | –CH₂–CH=CH₂ | –(CH₂)₅– | |
| CH₃ | CH₃ | H | S | S | –CH₂–C≡CH | –(CH₂)₅– | |
| CH₃ | CH₃ | H | S | S | –CH₂–C₆H₅ | –(CH₂)₅– | |
| CH₃ | CH₃ | 6-CH₃ | S | S | CH₃ | CH₃ | H |
| CH₃ | CH₃ | 6-CH₃ | S | S | C₂H₅ | CH₃ | H |
| CH₃ | CH₃ | 6-CH₃ | S | S | C₃H₇ | CH₃ | H |
| CH₃ | CH₃ | 6-CH₃ | S | S | i-C₃H₇ | CH₃ | H |
| CH₃ | CH₃ | 6-CH₃ | S | S | i-C₄H₉ | CH₃ | H |
| CH₃ | CH₃ | 6-CH₃ | S | S | s-C₄H₉ | CH₃ | H |
| CH₃ | CH₃ | 6-CH₃ | S | S | –CH₂–C(CH₃)₃ | CH₃ | H |
| CH₃ | CH₃ | 6-CH₃ | S | S | –(CH₂)₂–C(CH₃)₃ | CH₃ | H |
| CH₃ | CH₃ | 6-CH₃ | S | S | –CH₂–CH=CH₂ | CH₃ | H |
| CH₃ | CH₃ | 6-CH₃ | S | S | –CH₂–C≡CH | CH₃ | H |
| CH₃ | CH₃ | 6-CH₃ | S | S | –CH₂–C₆H₅ | CH₃ | H |
| CH₃ | CH₃ | 6-CH₃ | S | S | CH₃ | CH₃ | CH₃ |
| CH₃ | CH₃ | 6-CH₃ | S | S | C₂H₅ | CH₃ | CH₃ |
| CH₃ | CH₃ | 6-CH₃ | S | S | C₃H₇ | CH₃ | CH₃ |
| CH₃ | CH₃ | 6-CH₃ | S | S | i-C₃H₇ | CH₃ | CH₃ |
| CH₃ | CH₃ | 6-CH₃ | S | S | i-C₄H₉ | CH₃ | CH₃ |
| CH₃ | CH₃ | 6-CH₃ | S | S | s-C₄H₉ | CH₃ | CH₃ |
| CH₃ | CH₃ | 6-CH₃ | S | S | –CH₂–C(CH₃)₃ | CH₃ | CH₃ |
| CH₃ | CH₃ | 6-CH₃ | S | S | –(CH₂)₂–C(CH₃)₃ | CH₃ | CH₃ |
| CH₃ | CH₃ | 6-CH₃ | S | S | –CH₂–CH=CH₂ | CH₃ | CH₃ |
| CH₃ | CH₃ | H | S | S | –CH₂–C≡CH | CH₃ | CH₃ |
| CH₃ | CH₃ | H | S | S | –CH₂–C₆H₅ | CH₃ | CH₃ |
| CH₃ | CH₃ | 6-CH₃ | S | S | CH₃ | –(CH₂)₅– | |
| CH₃ | CH₃ | 6-CH₃ | S | S | C₂H₅ | –(CH₂)₅– | |
| CH₃ | CH₃ | 6-CH₃ | S | S | C₃H₇ | –(CH₂)₅– | |
| CH₃ | CH₃ | 6-CH₃ | S | S | i-C₃H₇ | –(CH₂)₅– | |
| CH₃ | CH₃ | 6-CH₃ | S | S | i-C₄H₉ | –(CH₂)₅– | |
| CH₃ | CH₃ | 6-CH₃ | S | S | s-C₄H₉ | –(CH₂)₅– | |
| CH₃ | CH₃ | 6-CH₃ | S | S | –CH₂–C(CH₃)₃ | –(CH₂)₅– | |
| CH₃ | CH₃ | 6-CH₃ | S | S | –(CH₂)₂–C(CH₃)₃ | –(CH₂)₅– | |
| CH₃ | CH₃ | 6-CH₃ | S | S | –CH₂–CH=CH₂ | –(CH₂)₅– | |
| CH₃ | CH₃ | 6-CH₃ | S | S | –CH₂–C≡CH | –(CH₂)₅– | |
| CH₃ | CH₃ | 6-CH₃ | S | S | –CH₂–C₆H₅ | –(CH₂)₅– | |

If, according to process (A), 3-(2,4-dimethylphenyl)-5-isopropyl-2,4-pyrrolidine-dione and 2,2,2-trifluoroethyl methanethiochlorophosphonate are used as starting materials, the course of the reaction can be represented by the following reaction scheme:

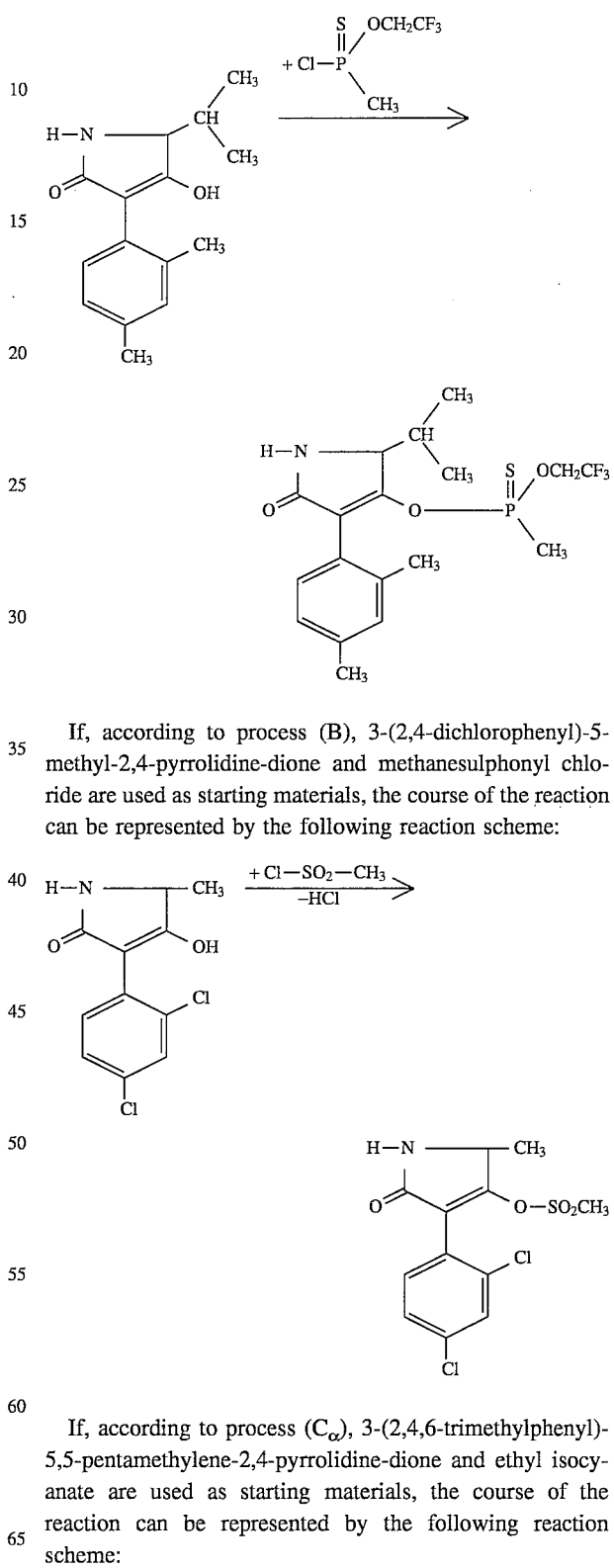

If, according to process (B), 3-(2,4-dichlorophenyl)-5-methyl-2,4-pyrrolidine-dione and methanesulphonyl chloride are used as starting materials, the course of the reaction can be represented by the following reaction scheme:

If, according to process ($C_\alpha$), 3-(2,4,6-trimethylphenyl)-5,5-pentamethylene-2,4-pyrrolidine-dione and ethyl isocyanate are used as starting materials, the course of the reaction can be represented by the following reaction scheme:

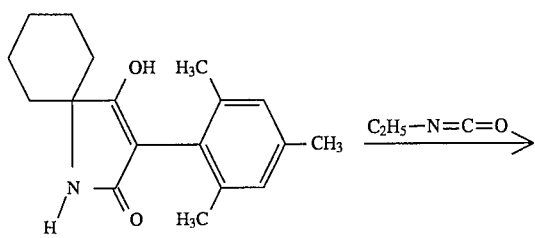

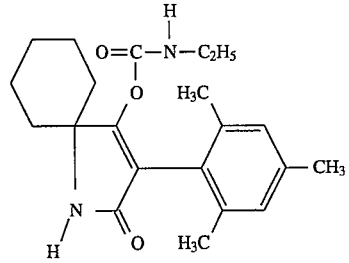

If, according to process (C$_\beta$), 3-(2,4,6-trimethylphenyl)-5-isopropyl-2,4-pyrrolidine-dione and dimethylcarbamoyl chloride are used as starting materials, the course of the reaction can be represented as follows:

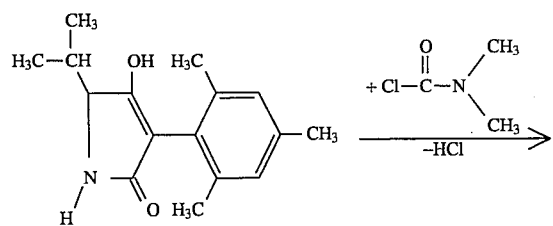

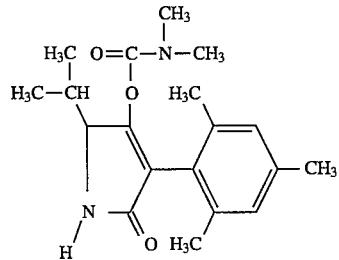

If, according to process (D$_\alpha$), 3-(2,4,6-trimethylphenyl)-5,5-dimethyl-2,4-pyrrolidine-dione and methyl chloromonothioformate are used as starting materials, the course of the reaction can be represented as follows:

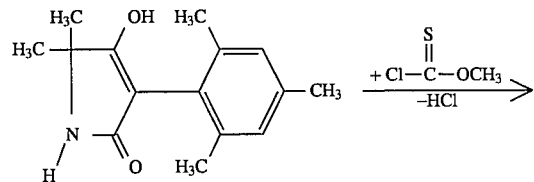

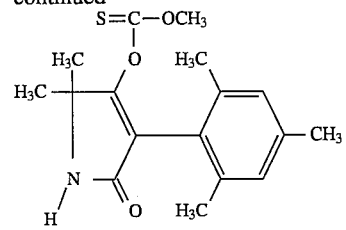

If, according to process (D$_\beta$), 3-(2,4,6-trimethylphenyl)-5,5-tetramethylene-2,4-pyrrolidine-dione, carbon disulphide and methyl iodide are used as starting components, the course of the reaction can be represented as follows:

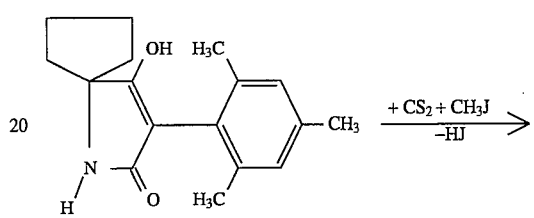

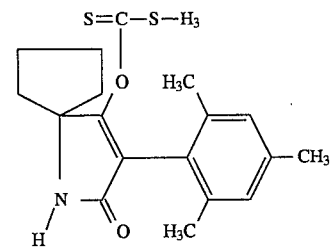

The compounds of the formula (II)

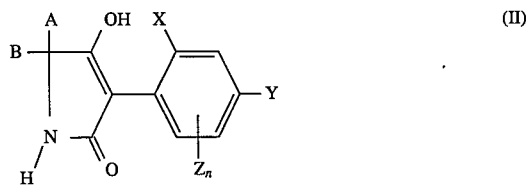

(II)

required as starting substances in the above process (A)–(D) in which A, B, X, Y, Z and n have the abovementioned meaning, are new but the subject of earlier applications by the Applicant Company. For example, compounds of the formula (II) are obtained when N-acylamino acid esters of the formula (IX)

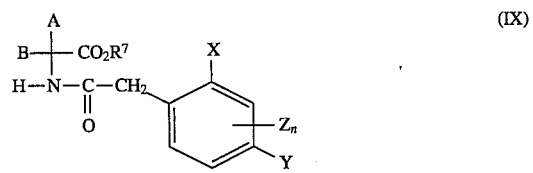

(IX)

in which A, B, X, Y, Z and n have the abovementioned meaning and R$^7$ represents alkyl, are subjected to an intramolecular condensation reaction in the presence of a diluent and in the presence of a base.

Some of the compounds of the formula (IX)

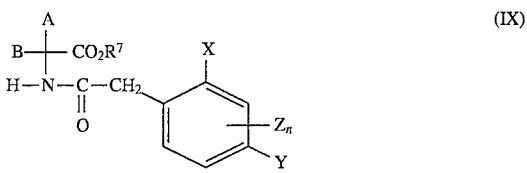

which are required as starting substances in the above process and in which A, B, X, Y, Z, n and $R^7$ have the abovementioned meaning, are known or can be prepared in a simple manner by methods known in principle. For example, acyl-amino acid esters of the formula (IX) are obtained when a) amino acid esters of the formula (X)

in which $R^4$ represents hydrogen (Xa) and alkyl (Xb) and
A and B have the abovementioned meaning, are acylated with phenylacetic acid halides of the formula (XI)

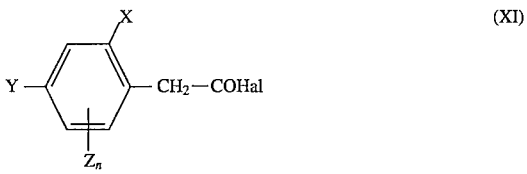

in which

X, Y, Z and n have the abovementioned meaning and
Hal represents chlorine or bromine (Chem. Reviews 52 237–416 (1953));

or when acylamino acids of the formula (IIa)

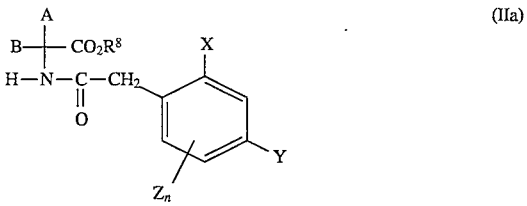

in which

A, B, X, Y, Z and n have the abovementioned meaning and
$R^8$ represents hydrogen, are esterified (Chem. Ind. (London) 1568 (1968)).

Following preparation process (A), to obtain compounds of the structure (Ia), 1 to 2, preferably 1 to 1.3, moles of the phosphorus compound of the formula (III) are reacted at temperatures between −40° and 150° C., preferably between −10° and 110° C., per mole of the compound (II).

Suitable diluents which may be added are all inert, polar organic solvents such as halogenated hydrocarbons, ethers, amides, nitriles, sulphides, sulphones, sulphoxides etc.

The following are preferably employed: acetonitrile, dimethyl sulphoxide, tetrahydrofuran, dimethylformamide and dimethyl sulphide.

Suitable acid-binding agents which may be added are customary inorganic or organic bases such as hydroxides or carbonates. Examples which may be listed are sodium hydroxide, sodium carbonate, potassium carbonate and pyridine.

The reaction can be carried out under atmospheric pressure or under increased pressure, it is preferably carried out under atmospheric pressure. Working-up is effected by customary methods of organic chemistry. The end products obtained are preferably purified by crystallisation, chromatographic purification or by so-called "incipient distillation", i.e. removal of the volatile components in vacuo.

Following preparation process (B), approx. 1 mole of sulphonyl chloride (IV) is reacted at 0° to 150° C., preferably 20° to 70° C., per mole of starting compound of the formula (II).

Suitable diluents which may be added are all inert polar organic solvents such as halogenated hydrocarbons, ethers, amides, nitriles, alcohols, sulphones and sulphoxides.

The following are preferably employed: methylene chloride, dimethyl sulphoxide, tetrahydrofuran, dimethylformamide and dimethyl sulphide.

If the enolate salt of the compound II is synthesised in a preferred embodiment by adding strong deprotonating agents (such as, for example, sodium hydride or potassium tertiary burylate), a further addition of acid-binding agents can be dispensed with.

If acid-binding agents are employed, then those which are suitable are customary inorganic or organic bases, examples which may be mentioned being sodium hydroxide, sodium carbonate, potassium carbonate and pyridine.

The reaction can be carried out under atmospheric pressure or under increased pressure, it is preferably carried out under atmospheric pressure. Working-up is carried out by customary methods.

If appropriate, the process following preparation process (B) can be carried out under phase-transfer conditions (W. J. Spillane et al., J. Chem. Soc. Perkin Trans I, (3) 677-9 (1982)). In this case, 0.3 to 1.5 moles of sulphonyl chloride (IV), preferably 0.5 mole, are reacted at 0° to 150° C., preferably 20° to 70° C., per mole of starting compound of the formula (II). Examples of phase-transfer catalysts which can be used are all quaternary ammonium salts, preferably tetraoctylammonium bromide and benzyltriethylammonium chloride. Organic solvents which can be used in this case are all unpolar inert solvents, benzene and toluene are preferably employed.

Following preparation process $(C_\alpha)$, approx. 1 mole of isocyanate of the formula (V) is reacted at 0° to 100° C., preferably at 20° to 50° C., per mole of starting compound of the formula (II).

Suitable diluents which may be added are all inert organic solvents such as ethers, amides, nitriles, sulphones or sulphoxides.

If appropriate, catalysts can be added to accelerate the reaction. Catalysts which are very advantageously employed are organotin compounds such as, for example, dibutyltin dilaurate. The process is preferably carried out under atmospheric pressure.

Following preparation process $(C_\beta)$, approx. 1 mole of carbamoyl chloride or thiocarbamoyl chloride of the formula (VI) is reacted at 0° to 150° C., preferably at 20° to 70° C., per mole of starting compound of the formula (II).

Suitable diluents which may be added are all inert polar organic solvents such as ethers, amides, alcohols, sulphones and sulphoxides.

The following are preferably employed: dimethyl sulphoxide, tetrahydrofuran, dimethylformamide and dimethyl sulphide.

If the enolate salt of the compound II is synthesised in a preferred embodiment by adding strong deprotonating agents (such as, for example, sodium hydride or potassium tertiary butylate), a further addition of acid-binding agents can be dispensed with.

If acid-binding agents are employed, then those which are suitable are customary inorganic or organic bases, examples which may be mentioned being sodium hydroxide, sodium carbonate, potassium carbonate and pyridine.

The reaction can be carried out under atmospheric pressure or under increased pressure, it is preferably carried out under atmospheric pressure. Working-up is carried out by customary methods.

Following preparation process ($D_\alpha$), approx. 1 mole of chloromonothioformic ester or chlorodithioformic ester of the formula (VII) is reacted at 0° to 120° C., preferably at 20° to 60° C., per mole of starting compound of the formula (II).

Suitable diluents which may be added are all inert organic solvents such as halogenated hydrocarbons, ethers, amides, alcohols, sulphones and sulphoxides.

The following are preferably employed: methylene chloride, dimethyl sulphoxide, tetrahydrofuran, dimethylformamide and dimethyl sulphide.

If the enolate salt of the compound II is synthesised in a preferred embodiment by adding strong deprotonating agents (such as, for example, sodium hydride or potassium tertiary butylate), a further addition of acid-binding agents can be dispensed with.

If acid-binding agents are employed, then those which are suitable are customary inorganic or organic bases, examples which may be mentioned being sodium hydroxide, sodium carbonate, potassium carbonate and pyridine.

The reaction can be carried out under atmospheric pressure or under increased pressure, it is preferably carried out under atmospheric pressure. Working-up is effected by customary methods.

Following preparation process ($D_\beta$), the equimolar amount, or an excess, of carbon disulphide is added per mole of starting compound of the formula (II). This process is preferably carried out at temperatures from 0° to 50° C. and, in particular, at 20° to 30° C.

It is frequently expedient to first prepare the corresponding salt from the compound of the formula (II) by adding a deprotonating agent (such as, for example, potassium tertiary butylate or sodium hydride). The compound (II) is reacted with carbon disulphide until the formation of the intermediate is complete, for example stirring at room temperature for several hours.

The further reaction with the alkyl halide of the formula (VIII) is preferably effected at 0° to 70° C. and, in particular, at 20° to 50° C. At least the equimolar amount of alkyl halide is employed in this process.

The process is carried out under atmospheric pressure or under increased pressure, preferably under atmospheric pressure.

Again, working-up is effected by customary methods.

The active compounds are suitable for combating animal pests, preferably arthropods and nematodes, in particular insects and arachnids, encountered in agriculture, in forestry, in the protection of stored products and of materials, and in the hygiene field. They are active against normally sensitive and resistant species and against all or some stages of development. The abovementioned pests include:

From the order of the Isopoda, for example, Oniscus asellus, *Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria*. From the order of the Dermaptera, for example, *Forficula auricularia*.

From the order of the Isoptera, for example, Reticulitermes spp. From the order of the Anoplura, for example, *Phylloxera vastatrix,* Pemphigus spp., Pediculus humanus corporis, Haematopinus spp. and Linognathus spp.

From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp. From the order of the Arachnida, for example, *Scorpio maurus* and *Latrodectus mactans*.

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp-, Hyalomma spp., Ixodes spp., psoroptes spp., Chorioptes spp., Sarcoptes spp., Tarsonemus spp., *Bryobia praetiosa,* Panonychus spp., Tetranychus spp.

The active compounds according to the invention are distinguished by a high insecticidal and acaricidal activity.

They can be employed particularly successfully against insects which are harmful to plants, such as, for example, against the larvae of the mustard beetle (*Phaedon cochleariae*) or against the larvae of the green rice cicada (*Nephotettix cinciteps*) or against mites which are harmful to plants such as, for example, against the common spider mite or the greenhouse red spider mite (*Tetranychus urticae*).

The active compounds according to the invention are not only active against plant, hygiene and stored product pests, but also, in the veterinary medicine sector, against animal parasites (ectoparasites and endoparasites) such as scaly ticks, argasidae, scab mites, trombidae, flies (biting and sucking), parasitic fly larvae, lice, hair lice, bird lice, fleas and endoparasitically living worms.

They are active against normally-sensitive and resistant species and strains and against all parasitising and non-parasitising development stages of the ecto- and endoparasites.

The active compounds according to the invention can furthermore be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quarts, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionogenic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and zinc.

The formulations in general contain between 0.1 and 95% by weight of active compound, preferably between 0.5 and 90%.

For combating weeds, the active compounds according to the invention, as such or in the form of their formulations, can also be used as mixtures with known herbicides, finished formulations or tank mixes being possible.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

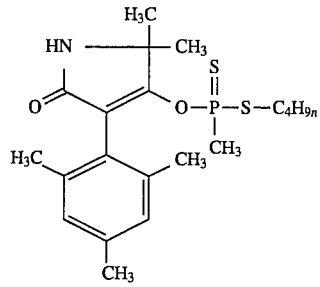

4 g (16.3 mmol) of 3-(2,4,6-trimethylphenyl)-5,5-dimethylpyrrolidine-2,4-dione are dissolved in 10 ml of are dissolved in 10 ml of tetrahydrofuran. To this solution there are added 2.5 ml (18 mmol) of triethylamine and then, at room temperature, 3.6 g (17.8 mmol) of S-(n-butyl) methanechlorodithiophosphonate. The batch is stirred at 50° C. for approx. two hours, and the end of the reaction is monitored chromatographically. After the solvent has been distilled off, the residue which remains is purified via a silica gel frit (mobile phase toluene:ethyl acetate 8:2).

1.6 g (29.2% of theory) of O-[3-(2,4,6-trimethylphenyl)-5,5-dimethylpyrrolidin-2-on-]S-(n-butyl) methanedithiophosphonate of melting point 98° C. are obtained.

EXAMPLE 2

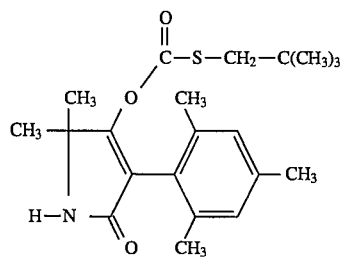

3.68 g (15 mmol) of 3-(2,4,6-trimethylphenyl)-5,5-dimethylpyrrolidine-2,4-dione are introduced into 60 ml of absolute methylene chloride. To this mixture there are added dropwise 2.3 ml (16.5 mmol) of triethylamine and then, at 0° to 10° C., 2.75 g (16.5 mmol) of S-(2,2-dimethylpropyl) chlorothiocarbonate, dissolved in 15 ml of absolute methylene chloride. The batch is stirred at room temperature for approx. 2 hours and the end of the reaction is monitored chromatographically. The reaction mixture is washed in succession with 10% strength citric acid, sodium hydrogen carbonate solution and sodium chloride solution, the organic phase is dried, and the solvent is distilled off. After recrystallisation from ethyl acetate/hexane 1:4, 2.74 g (49% of theory) of S-(2,2-dimethylpropyl) O-[3-(2,4,6-trimethylphenyl)-5,5-dimethylpyrrolidin-2-one]thiocarbonate of melting point 197°–200° C. are obtained.

EXAMPLE 3

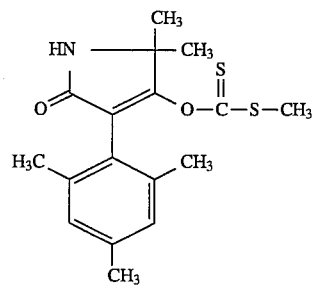

4.91 g (20 mmol) of 3-(2,4,6-trimethylphenyl)-5,5-dimethylpyrrolidine-2,4-dione are dissolved in 40 ml of anhydrous dimethylformamide. To this solution there are added 1.08 g of sodium methanolate, and stirring of the batch is continued for approx. 10 minutes. After an addition of 1.17 ml of carbon disulphide, the mixture is stirred for 3 hours at room temperature, and 1.24 ml of methyl iodide are subsequently added dropwise. The reaction batch is stirred at room temperature for another 3 hours, and the end of the reaction is monitored chromatographically. The reaction mixture is stirred into 120 ml of water, the precipitate is filtered off with suction, the filtrate is taken up in dichloromethane, and the mixture is washed with 200 ml of 0.5N sodium hydroxide solution. The organic phase is dried over magnesium sulphate and concentrated. 10 ml of ethyl acetate are used for making the crude product obtained into a paste under hot conditions, and the mixture is filtered off with suction. 2.1 g (31.3% of theory) of S-methyl O-[3-(2,4,6-trimethylphenyl)-5,5-dimethylpyrrolidin-2-one]thiocarbonate of melting point 214°–215° C. are obtained.

The end products of the formula (I) listed in Table 5 below are obtained in a manner analogous to that of Examples 1, 2 and 3 and having regard to the details in the description relating to the processes according to the invention.

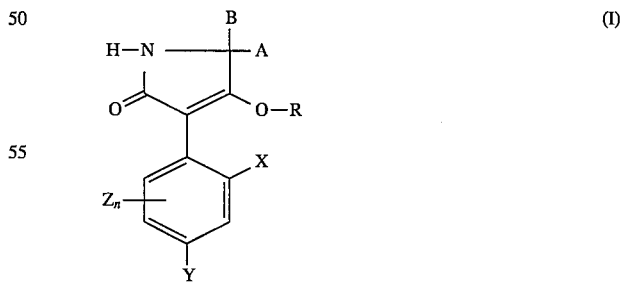
(I)

TABLE 5

| Ex. No. | A | B | X | Y | $Z_n$ | R | physical const. |
|---|---|---|---|---|---|---|---|
| 4 | $CH_3$ | $CH_3$ | $CH_3$ | $CH_3$ | 6-$CH_3$ | $-\overset{\overset{O}{\|}}{C}-S-(CH_2)_2-C(CH_3)_3$ | m.p.: 211° C. |
| 5 | $CH_3$ | $CH_3$ | $CH_3$ | $CH_3$ | 6-$CH_3$ | $-\overset{\overset{S}{\|}}{\underset{\underset{CH_3}{\|}}{P}}-S-C_4H_9 iso$ | m.p.: 104° C. |
| 6 | $CH_3$ | $CH_3$ | $CH_3$ | $CH_3$ | 6-$CH_3$ | $-SO_2-CH_3$ | m.p.: 194–195° C. |
| 7 | $CH_3$ | $CH_3$ | $CH_3$ | $CH_3$ | 6-$CH_3$ | $-SO_2-C_6H_5$ | m.p.: 217–218° C. |
| 8 | $CH_3$ | $CH_3$ | $CH_3$ | $CH_3$ | 6-$CH_3$ | $-SO_2-C_3H_7 iso$ | m.p.: 187–193° C. |
| 9 | $CH_3$ | $CH_3$ | $CH_3$ | $CH_3$ | 6-$CH_3$ | $-\overset{\overset{O}{\|}}{C}-N(morpholino)$ | m.p.: 96–105° C. |
| 10 | $-(CH_2)_5-$ | | $CH_3$ | $CH_3$ | 6-$CH_3$ | $-SO_2-CH_3$ | m.p.: 201–206° C. |
| 11 | $CH_3$ | $CH_3$ | $CH_3$ | $CH_3$ | 6-$CH_3$ | $-\overset{\overset{O}{\|}}{C}-SC_3H_7 iso$ | m.p. 180–186° C. |
| 12 | $CH_3$ | $CH_3$ | $CH_3$ | $CH_3$ | 6-$CH_3$ | $-\overset{\overset{O}{\|}}{C}-SC_4H_9 tert.$ | m.p. 184–188° C. |
| 13 | $CH_3$ | $CH_3$ | $CH_3$ | $CH_3$ | 6-$CH_3$ | $-\overset{\overset{O}{\|}}{C}-SCH_2CH_2-CH(CH_3)_2$ | m.p. 132–135° C. |
| 14 | $-(CH_2)_5-$ | | $CH_3$ | $CH_3$ | 6-$CH_3$ | $-\overset{\overset{O}{\|}}{C}-SC_3H_7 iso$ | m.p. 193–196° C. |
| 15 | $-(CH_2)_5-$ | | $CH_3$ | $CH_3$ | 6-$CH_3$ | $-\overset{\overset{O}{\|}}{C}-SCH_2-C(CH_3)_3$ | m.p. 252–260° C. |
| 16 | $CH_3$ | $CH_3$ | $CH_3$ | $CH_3$ | 6-$CH_3$ | $-C-SCH(CH_3)-CH_2-CH(CH_3)$ | m.p. 126–128° C. |
| 17 | $C_3H_7 iso$ | H | $CH_3$ | $CH_3$ | 6-$CH_3$ | $-\overset{\overset{O}{\|}}{C}-S-CH_2-C(CH_3)_3$ | m.p. 138–139° C. |
| 18 | $C_3H_7 iso$ | H | $CH_3$ | $CH_3$ | 6-$CH_3$ | $-\overset{\overset{O}{\|}}{C}-S-CH_2-CH_2-C(CH_3)_3$ | m.p. 64–66° C. |
| 19 | $C_3H_7 iso$ | H | $CH_3$ | $CH_3$ | 6-$CH_3$ | $-\overset{\overset{O}{\|}}{C}-SC_3H_7 iso$ | m.p. 160–161° C. |
| 20 | $C_3H_7 iso$ | H | $CH_3$ | $CH_3$ | 6-$CH_3$ | $-\overset{\overset{O}{\|}}{C}-S-CH(CH_3)-CH_2-CH(CH_3)_2$ | m.p. 127–128° C. |
| 21 | $CH_3$ | $CH_3$ | $CH_3$ | $CH_3$ | 6-$CH_3$ | $-\overset{\overset{S}{\|}}{\underset{\underset{CH_3}{\|}}{P}}-O-CH(CH_3)-C_2H_5$ | m.p. 138° C. |
| 22 | $CH_3$ | $CH_3$ | $CH_3$ | $CH_3$ | 6-$CH_3$ | $-\overset{\overset{S}{\|}}{\underset{\underset{CH_3}{\|}}{P}}-OC_3H_7 iso$ | m.p. 150° C. |

TABLE 5-continued

| Ex. No. | A | B | X | Y | $Z_n$ | R | physical const. |
|---|---|---|---|---|---|---|---|
| 23 | $CH_3$ | $CH_3$ | $CH_3$ | $CH_3$ | 6-$CH_3$ | $-\overset{\overset{S}{\|}}{\underset{CH_3}{P}}-OC_2H_5$ | m.p. 160° C. |
| 24 | $CH_3$ | $CH_3$ | $CH_3$ | $CH_3$ | 6-$CH_3$ | $-\overset{\overset{S}{\|}}{\underset{OC_2H_5}{P}}-OC_2H_5$ | m.p. 143° C. |
| 25 | $CH_3$ | $CH_3$ | $CH_3$ | $CH_3$ | 6-$CH_3$ | $-\overset{\overset{S}{\|}}{\underset{CH_3}{P}}-OCH_2-C(CH_3)_3$ | m.p. 107° C. |

Use Examples

In the Use Examples which follow, the compounds listed below were employed as comparison substances:

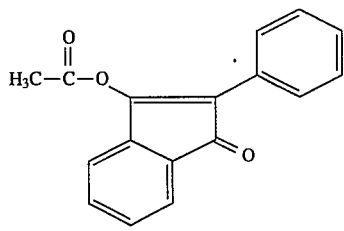

(A)

3-(Acetyloxy)-2-phenyl-1H-inden-1-one (disclosed in U.S. Pat. No. 4,104,043)

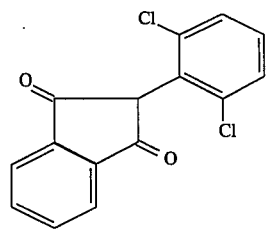

(B)

2-(2,6-Dichlorophenyl)-1H-inden-1,3(2H)-dione (disclosed in U.S. Pat. No. 3,954,998)

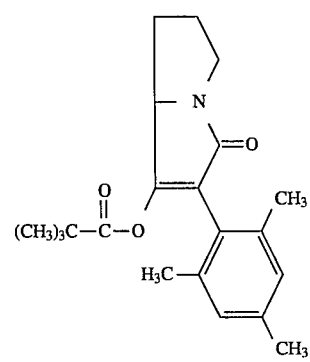

(C)

2,2-Dimethyl-2,3,5,7a-tetrahydro-5-oxo-6-(2,4,6-trimethylphenyl)-1H-pyrrolidin-7-yl propionate (disclosed in EP-A 355,599).

Example A

Tetranychus test (OP resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the common spider mite or greenhouse red spider mite (*Tetranychus urticae*) are treated by being dipped into the active compound preparation of the desired concentration.

After the desired period, the destruction is determined in %. 100% means that all spider mites have been destroyed; 0% means that no spider mites have been destroyed.

In this test, a superior activity compared with the prior art is shown, for example, by the following compounds of the Preparation Examples: 1, 2 and 5.

Example B

Nephotettix test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the active compound preparation of the desired concentration and infested with the green rice cicada (*Nephotettix cincticeps*) while the seedlings are still moist.

After the desired period, the destruction is determined in %. 100% means that all cicadae have been destroyed; 0% means that no cicadae have been destroyed.

In this test, a superior activity compared with the prior art is shown, for example, by the following compounds of the Preparation Examples: 1, 2 and 5.

Example C

Phaedon larvae test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and 100%=total destruction.

In this test, a superior activity with the prior art is shown, for example, by the compound of Preparation Example 2.

| Active compound | PRE-EMERGENCE-TEST/GREENHOUSE | | | | | | |
|---|---|---|---|---|---|---|---|
| | amount of active compound g/ha | Cotton | Alspecurus | Digitaria | Echinochloa | Setaria | Sorghum |
| (B) known compound disclosed in U.S. Pat. No. 3,954,998 | 1000 | 60 | 50 | 40 | 50 | 70 | 0 |
| (2) | 500 | 0 | 80 | 90 | 95 | 100 | 95 | the concentrate is diluted with water to the desired concentration.

Cabbage leaves (*Brassica oleracea*) are treated by being dipped into the active compound preparation of the desired concentration and infested with mustard beetle larvae (*Phaedon cochleariae*) while the seedlings are still moist.

After the desired period, the destruction is determined in %. 100% means that all beetle larvae have been destroyed; 0% means that no beetle larvae have been destroyed.

In this test, a superior activity compared with the prior art is shown, for example, by the following compounds of the Preparation Examples: 1, 2, 4 and 5.

Example

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

We claim:

1. A substituted 3-aryl-pyrrolidine-2,4-dione derivative of the general formula

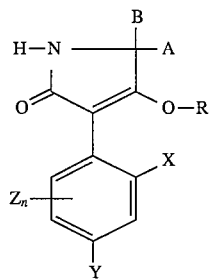

(I)

in which

X represents $C_{1-6}$-alkyl,

Y represents $C_{1-6}$-alkyl,

Z represents $C_{1-6}$-alkyl, n represents a number from 0–3,

A and B independently represent hydrogen, or $C_{1-4}$-alkyl, or in which

A and B together with the carbon atom to which they are bonded represent cyclohexyl, R represents

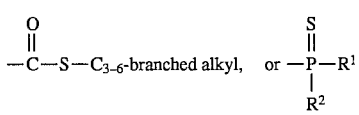

in which

R$^1$ and R$^2$ independently of each other represent C$_1$–C$_6$-alkyl, C$_1$–C$_6$-alkoxy or C$_1$–C$_6$-alkylthio, and the pure enantiomeric forms of compounds of the formula (I).

2. A compound according to claim 1, of the formula

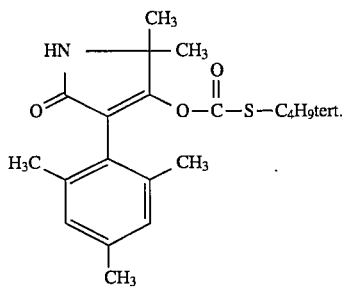

3. A compound selected from the group consisting of

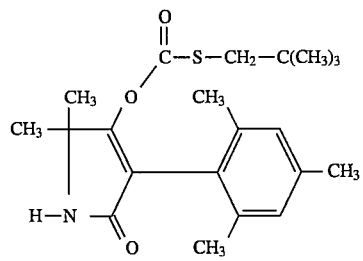

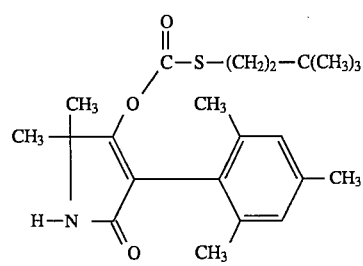

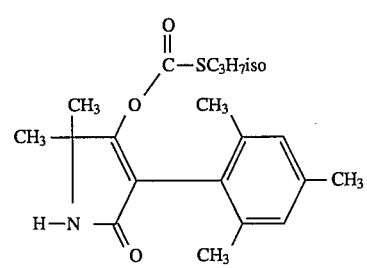

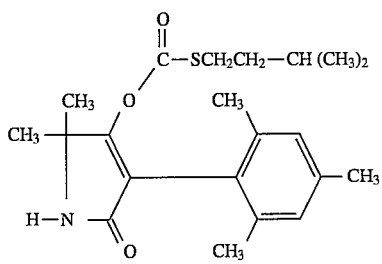

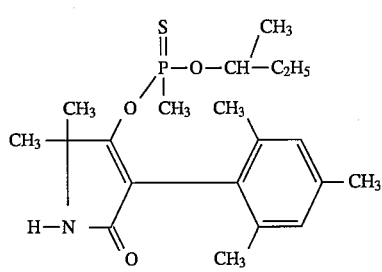

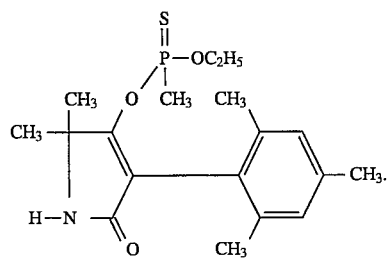

4. A compound according to claim 3 in a pure enantiomeric form.

5. A compound according to claim 4, of the formula

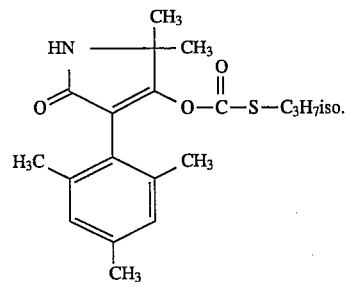

6. A compound according to claim 5 in a pure enantiomeric form.

7. Insecticidal, acaricidal and herbicidal compositions, characterized in that they contain at least one 3-aryl-pyrrolidine-2,4-dione derivatives of the formula (I) according to claim 1.

8. Method of combating insects and/or arachnids and/or weeds, characterized in that 3-aryl-pyrrolidine-2,4-dione derivatives of the formula (I) according to claim 1 are allowed to act on insects and/or arachnids and/or weeds and/or their environment.

* * * * *